(12) United States Patent
Brunette et al.

(10) Patent No.: US 7,468,382 B2
(45) Date of Patent: Dec. 23, 2008

(54) PYRIDINE DERIVATIVES USEFUL AS INHIBITORS OF PKC-THETA

(75) Inventors: Steven Richard Brunette, New Milford, CT (US); Jin Mi Kim, Sandy Hook, CT (US); Rene' Marc Lemieux, Plantsville, CT (US); Matt Aaron Tschantz, Newtown, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 304 days.

(21) Appl. No.: 11/277,536

(22) Filed: Mar. 27, 2006

(65) Prior Publication Data

US 2006/0217417 A1  Sep. 28, 2006

Related U.S. Application Data

(60) Provisional application No. 60/665,748, filed on Mar. 28, 2005.

(51) Int. Cl.
*A01N 43/40* (2006.01)
*A61K 31/44* (2006.01)
*C07D 211/72* (2006.01)
*C07D 211/84* (2006.01)
*C07D 213/00* (2006.01)
*C07D 213/72* (2006.01)

(52) U.S. Cl. .................. 514/346; 514/352; 546/292; 546/304

(58) Field of Classification Search .............. 546/292, 546/304; 514/346, 352
See application file for complete search history.

(56) References Cited

U.S. PATENT DOCUMENTS 3,929,785 A * 12/1975 Ramanathan ............... 544/184

2004/0242613 A1   12/2004  Cardozo

FOREIGN PATENT DOCUMENTS

WO    WO 03/106451 A1   12/2003

OTHER PUBLICATIONS

Marsland et al., J. Exp. Med., 2004, vol. 200, pp. 181-189.*

* cited by examiner

*Primary Examiner*—D. Margaret Seaman
*Assistant Examiner*—Niloofar Rahmani
(74) *Attorney, Agent, or Firm*—Michael P. Morris; Mary-Ellen M. Devlin; Philip I. Datlow

(57) ABSTRACT

Disclosed are novel compounds of formula (I):

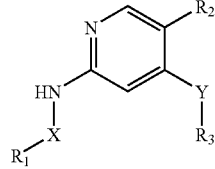

wherein $R_1$, $R_2$ and $R_3$ are as defined herein, which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

6 Claims, No Drawings

PYRIDINE DERIVATIVES USEFUL AS INHIBITORS OF PKC-THETA

CROSS-REFERENCE TO RELATED APPLICATIONS

This application claims benefit to U.S. Provisional Application No. 60/665,748, filed Mar. 28, 2005.

FIELD OF THE INVENTION

This invention relates to substituted pyridine derivatives which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

BACKGROUND OF THE INVENTION

The protein kinase C family is a group of serine/threonine kinases that is comprised of twelve related isoenzymes. These kinases are expressed in a wide range of tissues and cell types. Its members are encoded by different genes and are sub-classified according to their requirements for activation. The classical PKC enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKC-theta is a member of the nPKC sub-family. It has a restricted expression pattern, found predominantly in T cells and skeletal muscle. Upon T cell activation, a supramolecular activation complex (SMAC) forms at the site of contact between the T cell and antigen presenting cell (APC). PKC-theta is the only PKC isoform found to localize at the SMAC (C. Monks et al., *Nature*, 1997, 385, 83), placing it in proximity with other signaling enzymes that mediate T cell activation processes. In another study (G. Baier-Bitterlich et al., *Mol. Cell. Biol.*, 1996, 16, 842) the role of PKC-theta in the activation of AP-1, a transcription factor important in the activation of the IL-2 gene, was confirmed. In unstimulated T cells, constitutively active PKC-theta stimulated AP-1 activity while in cells with dominant negative PKC-theta, AP-1 activity was not induced upon activation by PMA. Other studies showed that PKC-theta, via activation of IKB kinase beta, mediates activation of NF-κB induced by T cell receptor/CD28 co-stimulation (N. Coudronniere et al., *Proc. Nat. Acad. Sci. U.S.A.*, 2000, 97, 3394; X. Lin et al., *Moll. Cell. Biol.*, 2000, 20, 2933). Proliferation of peripheral T cells from PKC-theta knockout mice, in response to T cell receptor (TCR)/CD28 stimulation was greatly diminished compared to T cells from wild type mice. In addition, the amount of IL-2 released from the T cells was also greatly reduced (Z. Sun et al., *Nature*, 2000, 404, 402). Otherwise, the PKC-theta knockout mice seemed normal and were fertile.

The studies cited above and other studies confirm the critical role of PKC-theta in T cell activation and subsequent release of cytokines such as IL-2 and T cell proliferation (A. Altman et al., *Immunology Today*, 2000, 21, 567). Thus an inhibitor of PKC-theta would be of therapeutic benefit in treating immunological disorders and other diseases mediated by the inappropriate activation of T cells.

It has been well established that T cells play an important role in regulating the immune response (Powrie and Coffman, *Immunolog Today*, 1993, 14, 270). Indeed, activation of T cells is often the initiating event in immunological disorders. Following activation of the TCR, there is an influx of calcium that is required for T cell activation. Upon activation, T cells produce cytokines, including IL-2, leading to T cell proliferation, differentiation, and effector function. Clinical studies with inhibitors of IL-2 have shown that interference with T cell activation and proliferation effectively suppresses immune response in vivo (Waldmann, *Immunology Today*, 1993, 14, 264). Accordingly, agents that inhibit T lymphocyte activation and subsequent cytokine production are therapeutically useful for selectively suppressing the immune response in a patient in need of such immunosuppression and therefore are useful in treating immunological disorders such as autoimmune and inflammatory diseases.

In addition, PKC-theta activation has been shown to be associated with insulin resistance in skeletal muscle (M. E. Griffen et al., *Diabetes*, 1999, 48, 1270). Therefore inhibitors of PKC-theta may also be useful for treating type II diabetes.

Cardozo et al, U.S. Publication No. 2004/0242613 A1 discloses 2,4-diaminopyrimidine derivatives as inhibitors of PKC-theta. WO 03/106451 discloses certain substituted diaminopyrimidine compounds as inhibitors of PKC-theta. WO 04/065378 discloses certain 2-aminopyridine compounds as cyclin-dependent kinase 4 (CDK/4) inhibitors useful in the treatment of cell proliferative diseases. WO 04/011456 discloses certain substituted 2,4-diaminopyridine compounds as protein tyrosine kinase inhibitors.

There is a continuing need in the art for compounds that are potent and selective inhibitors of PKC-theta.

BRIEF SUMMARY OF THE INVENTION

In a general aspect, the present invention is directed to the compounds of the following formula (I):

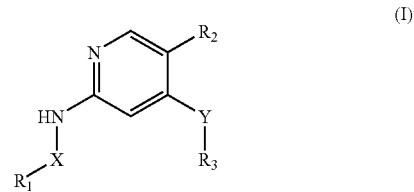

wherein X, Y, $R_1$, $R_2$ and $R_3$ are as defined herein, as well as the tautomers, pharmaceutically acceptable salts, solvates, and amino-protected derivatives thereof. It has been found that the compounds of formula (I) have valuable pharmacological properties, particularly an inhibiting activity on PKC-theta. Many of the compounds of the invention are not only potent inhibitors of PKC-theta but are also selective for the inhibition of PKC-theta as compared to one or more other protein kinases.

In another aspect, the present invention is directed to a method of inhibiting PKC-theta activity in a patient comprising administering to the patient a compound of the present invention as described above.

In another aspect, the present invention is directed to a method of treating a disease or disorder associated with the activation of T cells comprising administering to a patient in need of such treatment a compound of the present invention as described above.

In another aspect, the present invention is directed to a method of treating an immunological disorder comprising administering to a patient in need of such treatment a compound of the present invention as described above. Examples of such immunological disorders that may be treated include, for example, inflammatory diseases, autoimmune diseases, organ and bone marrow transplant rejection and other disorders associated with T cell mediated immune response, including acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus.

In another aspect, the present invention is directed to a method of treating type II diabetes comprising administering to a patient in need of such treatment a compound of the present invention as described above.

In yet additional aspects, the present invention is directed to pharmaceutical compositions comprising the above-mentioned compounds, processes for preparing the above-mentioned compounds and intermediates used in these processes.

DETAILED DESCRIPTION OF THE INVENTION

Definition of Terms and Conventions Used

Terms not specifically defined herein should be given the meanings that would be given to them by one of skill in the art in light of the disclosure and the context. As used in the present specification and claims, however, unless specified to the contrary, the following terms have the meaning indicated and the following conventions are adhered to.

A. Chemical Nomenclature, Terms, and Conventions

In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk-(where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

All references to a chemical group being "substituted with" another chemical group shall be understood to mean the first chemical group can be substituted with one or more of the second chemical group, with the exception of any substitution pattern that is not physically or chemically possible or results in a unstable structure or compound. For example, the phrase "$C_{1-6}$ alkyl, which is optionally substituted with halogen" shall mean a $C_{1-6}$ alkyl group having one or multiple halogen substituents being the same or different from each other.

All alkyl groups shall be understood as being branched or unbranched unless otherwise specified. Other more specific definitions are as follows:

The term "halogen" as used in the present specification shall be understood to mean bromine, chlorine, fluorine or iodine.

The term "heteroaryl" refers to a stable 5 or 6 membered, monocyclic aromatic heterocycle radical, wherein the heterocycle radical is optionally fused to either an aryl, e.g. benzene, or to a second 5 or 6 membered, monocyclic aromatic heterocycle to form in each case a bicyclic heteroaryl group. Each heterocycle consists of carbon atoms and from 1 to 3 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl.

The term "aryl" shall be understood to mean a 6-10 membered monocyclic or bicyclic aromatic carbocycle, and includes, for example, phenyl and naphthyl; other terms comprising "aryl" will have the same definition for the aryl component, and examples of these moieties include: arylalkyl, aryloxy or arylthio.

The term "oxo" refers to a double-bonded oxygen group (=O).

The phrases "wherein each of the $C_{1-6}$ alkyl groups", "wherein each of the $C_{1-8}$ alkyl groups" or "wherein each of the aryl groups" or similar language in a definition is intended to refer to the indicated groups when either alone or as part of another chemical group if such combined groups are provided for in a definition. For example, the language "wherein each of the $C_{1-6}$ alkyl groups" refers to $C_{1-6}$ alkyl groups as well as $C_{1-6}$ alkyl groups when attached to other groups, e.g., the $C_{1-6}$ alkyl portion of a $C_{1-6}$ alkyloxy or aryl-$C_{1-6}$ alkyl group, if such groups are provided for in a definition.

The term "amino protected derivatives" shall be understood to mean compounds of formula (I) wherein one or more of the amine groups are protected by suitable amino protecting groups. Amino protecting groups that may be used include, for example, alkoxycarbonyl groups, such as tert-butyloxycarbonyl (Boc) and ethoxycarbonyl, Mannich bases, Schiff bases and amino acids. As would be understood by a person skilled in the art, such amino protected compounds may be useful as intermediates in the preparation of other compounds of formula (I), e.g., as described in the synthetic processes below, and/or may themselves be useful as prodrugs that can be administered to a patient to be converted in vivo into a PKC-theta inhibitor having the resulting pharmacologic and therapeutic effects expected from the inhibition of PKC-theta in a patient.

The term "pharmaceutically acceptable salts" include those derived from pharmaceutically acceptable inorganic and organic acids and bases. Examples of suitable acids include hydrochloric, hydrobromic, carbonic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_{1-4}$ alkyl)$_4^+$ salts.

The term "solvate" means a physical association of a compound with one or more solvent molecules or a complex of variable stoichiometry formed by a solute (for example, a compound of Formula (I)) and a solvent, for example, water, EtOH, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, EtOHates, MeOHates, and the like.

The term "hydrate" means a solvate wherein the solvent molecule(s) is/are $H_2O$.

The term "compounds of the invention" and equivalent expressions are meant to embrace compounds of Formula (I) as herein described, including the tautomers, pharmaceutically acceptable salts, solvates, and amino-protected derivatives thereof, where the context so permits. In general, the compounds of the invention and the formulas designating the compounds of the invention are understood to only include the stable compounds thereof and exclude unstable compounds, even if an unstable compound might be considered to be literally embraced by the compound formula.

The term "stable compound" means a compound that is sufficiently robust to survive isolation to a useful degree of purity from a reaction mixture, and formulation into an efficacious therapeutic agent. For example, a compound which would have a "dangling valency" is not a compound contemplated by the invention.

Specific compounds of the present invention may be identified in the present specification by chemical name and/or chemical structure. In the event of any conflict between the chemical name and chemical structure, the chemical structure will control.

B. Isomer Terms and Conventions

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

C. Pharmaceutical Administration Terms and Conventions

The term "patient" includes both human and non-human mammals.

The term "therapeutically effective amount" means an amount of a compound according to the invention which, when administered to a patient in need thereof, is sufficient to effect treatment for disease-states, conditions, or disorders for which the compounds have utility.

Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the state of the art, and this disclosure.

The phrase "disease or disorder associated with the activation of T cells" and similar expressions mean that the activation of T cells is a contributing factor to either the origin or continuation of the disease or disorder in the patient.

Embodiments of the Invention

In its broadest generic aspect the invention provides novel compounds of formula (I) as described below:

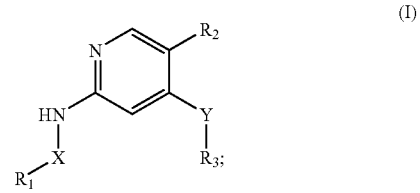

wherein:
X is a bond or $C_{1-6}$alkyl wherein one or two of the methylene units can be replaced by an oxygen or sulfur atom, and wherein the $C_{1-6}$alkyl group is optionally and independently substituted with:
  (A) oxo,
  (B) $C_{1-6}$alkyl which is optionally substituted with one or more of the following groups:
    (i) hydroxyl,
    (ii) $C_{1-6}$alkyloxy,
    (iii) $C_{1-6}$alkylthio,
    (iv) halogen,
  (C) —$COR_6$, wherein $R_6$ is:
    (i) $C_{1-6}$alkyl,
    (ii) $C_{1-6}$alkyloxy, (iii) —NR$_7$R$_8$, wherein R$_7$ and R$_8$ are each independently selected from:
   (a) hydrogen,
   (b) C$_{1-6}$alkyl,
   (c) aryl,
   (d) heteroaryl,
   (e) or wherein R$_7$ and R$_8$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;
(D) —OH,
(E) halogen,
(F) —NR$_9$R$_{10}$, wherein R$_9$ and R$_{10}$ are each independently selected from:
   (i) hydrogen,
   (ii) C$_{1-6}$alkyl, optionally substituted with C$_{1-6}$alkyloxy,
   (iii) C$_{1-6}$alkylcarbonyl,
   (iv) C$_{1-6}$alkylsulfonyl,
   (v) aryl,
   (vi) heteroaryl,
   (vii) or wherein R$_9$ and R$_{10}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;
Y is —NH—, —O— or —S—;
R$_1$ is a C$_{3-6}$cycloalkyl, aryl or heteroaryl, each of which is optionally and independently substituted with one or more of the following groups:
(A) C$_{1-6}$alkyl, which is optionally substituted with one or more of the following groups:
   (i) halogen,
   (ii) hydroxyl,
   (iii) amino, which is optionally substituted with C$_{1-6}$alkyl,
(B) C$_{1-6}$alkyloxy, which is optionally substituted with halogen,
(C) C$_{1-6}$alkylthio, which is optionally substituted with halogen,
(D) C$_{1-6}$alkylsulfonyl,
(E) cyano,
(F) halogen,
(G) hydroxyl,
(H) nitro,
(I) —NR$_{11}$R$_{12}$, wherein R$_{11}$ and R$_{12}$ are each independently selected from:
   (i) hydrogen,
   (ii) C$_{1-6}$alkyl,
   (iii) C$_{1-6}$alkylcarbonyl,
   (iv) C$_{1-6}$alkylsulfonyl,
   (v) or wherein R$_{11}$ and R$_{12}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;
(J) —COR$_{13}$, wherein R$_{13}$ is:
   (i) C$_{1-6}$alkyl
   (ii) C$_{1-6}$alkyloxy,
   (iii) —OH,
   (iv) —NR$_{14}$R$_{15}$, wherein R$_{14}$ and R$_{15}$ are each independently selected from:
      (a) hydrogen,
      (b) C$_{1-6}$alkyl,
      (c) or wherein R$_{14}$ and R$_{15}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;
(K) —O—R$_{16}$, —S—R$_{16}$, or —SO$_2$—R$_{16}$, wherein R$_{16}$ is aryl or heteroaryl optionally and independently substituted with one or more of the following groups:
   (i) C$_{1-6}$alkyl,
   (ii) C$_{1-6}$alkyloxy,
   (iii) —OH,
   (iv) —NR$_{17}$R$_{18}$, wherein R$_{17}$ and R$_{18}$ are each independently selected from:
      (a) hydrogen,
      (b) C$_{1-6}$alkyl,
      (c) C$_{1-6}$alkylcarbonyl,
      (d) C$_{1-6}$alkylsulfonyl,
   (v) C$_{1-6}$alkylthio,
   (vi) C$_{1-6}$alkylcarbonyl,
   (vii) C$_{1-6}$alkylsulfonyl,
   (viii) cyano,
   (ix) halogen,
   (x) nitro;
R$_2$ is selected from the following groups:
   (A) —CF$_3$,
   (B) cyano,
   (C) —CONH$_2$,
   (D) halogen, or
   (E) nitro;
R$_3$ is:

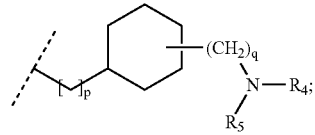

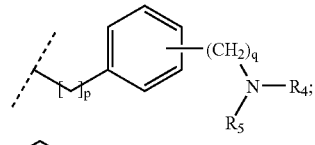

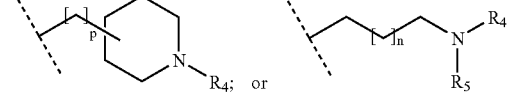

wherein:
p is an integer from 1 to 3;
q is an integer from 0 to 3;
n is an integer from 0 to 5;
R$_4$, R$_5$ are each independently selected from:
   (A) hydrogen,
   (B) C$_{1-6}$alkyl optionally and independently substituted with one or more of the following groups (i) to (ix), or wherein R$_4$ and R$_5$ together constitute a methylene bridge which together with the nitrogen atom between them forms a four to six-membered ring wherein one of the methylene groups is optionally replaced by an oxygen, sulfur or NR group, wherein R is hydrogen or C$_{1-6}$alkyl, and said ring is optionally substituted with one or more of the following groups (i) to (ix):
      (i) hydroxyl,
      (ii) C$_{1-6}$alkyloxy,
      (iii) C$_{1-6}$alkylthio, (iv) halogen,
(v) aryl,
(vi) heteroaryl,
(vii) —COR$_{19}$, wherein R$_{19}$ is:
  (a) C$_{1-6}$alkyl,
  (b) C$_{1-6}$alkyloxy,
  (c) —NR$_{20}$R$_{21}$, wherein R$_{20}$ and R$_{21}$ are each independently selected from:
    (I) hydrogen,
    (II) C$_{1-6}$alkyl,
    (III) aryl,
    (IV) heteroaryl
    (V) or wherein R$_{20}$ and R$_{21}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl,
(viii) —SO$_2$R$_{22}$, wherein R$_{22}$ is selected from:
  (a) C$_{1-6}$alkyl,
  (b) aryl,
  (c) —NR$_{23}$R$_{24}$, wherein R$_{23}$ and R$_{24}$ are each independently selected from:
    (I) hydrogen,
    (II) C$_{1-6}$alkyl,
    (III) aryl,
    (IV) heteroaryl,
(ix) —NR$_{25}$R$_{26}$, wherein R$_{25}$ and R$_{26}$ are each independently selected from:
  (a) hydrogen,
  (b) C$_{1-6}$alkyl,
  (c) aryl,
  (d) heteroaryl,
  (e) —COR$_{27}$, wherein R$_{27}$ is:
    (I) C$_{1-6}$alkyl,
    (II) C$_{1-6}$alkyloxy,
    (III) —NR$_{28}$R$_{29}$, wherein R$_{28}$ and R$_{29}$ are each independently selected from:
      (1) hydrogen,
      (2) C$_{1-6}$alkyl,
      (3) aryl,
      (4) heteroaryl, and
      (5) or wherein R$_{28}$ and R$_{29}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;
  (f) —SO$_2$R$_{30}$, wherein R$_{30}$ is selected from:
    (I) C$_{1-6}$alkyl,
    (II) aryl, and
    (III) heteroaryl, or a tautomer, pharmaceutically acceptable salt, solvate or amino-protected derivative thereof In another embodiment there are provided compounds of formula (I) as described above and wherein:
X is —CH$_2$—, —CH$_2$—CH$_2$— or —CH$_2$—CH$_2$—CH$_2$—;
Y is —NH—;
R$_1$ is selected from aryl optionally and independently substituted with one or more of the following groups:
(A) C$_{1-6}$alkoxy or C$_{1-6}$alkylthio, each optionally substituted with halogen,
(B) halogen, R$_2$ is selected from the following groups:
(A) cyano,
(B) —CONH$_2$, or
(C) nitro;
R$_3$ is:

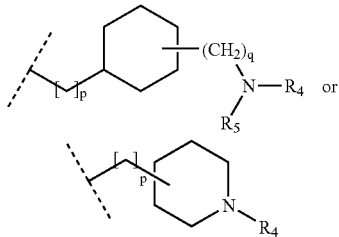

wherein:
p is 1 or 2,
q is 0, 1 or 2,
R$_4$, R$_5$ are hydrogen or C$_{1-6}$alkyl, or wherein R$_4$ and R$_5$ together constitute a methylene bridge which together with the nitrogen atom between them forms a four or five-membered ring which is optionally and independently substituted with a hydroxyl group;

or a tautomer, pharmaceutically acceptable salt, solvate or amino-protected derivative thereof.

In another embodiment there are provided compounds of formula (II) wherein:

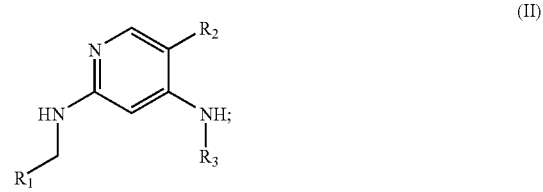

R$_1$ is phenyl, optionally and independently substituted with one or two of the following groups:
(A) —OCF$_3$,
(B) halogen,
R$_2$ is selected from the following groups:
(A) cyano, or
(B) nitro;
R$_3$ is:

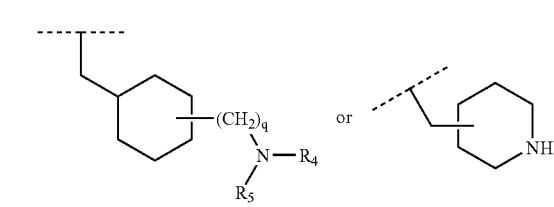

wherein:
q is 0 or 1,
R$_4$, R$_5$ are hydrogen or, wherein R$_4$ and R$_5$ together constitute a methylene bridge which together with the nitrogen atom between them forms a four or five-membered ring which is optionally substituted with a hydroxyl group, or a tautomer, pharmaceutically acceptable salt, solvate or amino-protected derivative thereof.

In another embodiment there are provided compounds of formula (III) wherein:

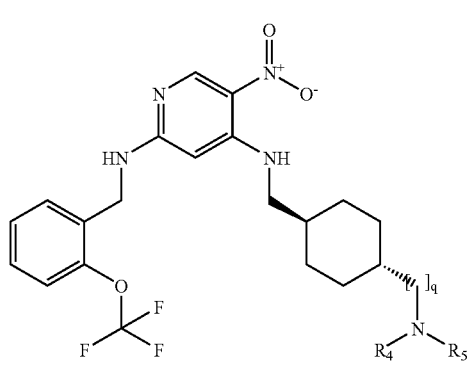

q is 0 or 1,
R$_4$, R$_5$ are hydrogen or wherein R$_4$ and R$_5$ together constitute a methylene bridge which together with the nitrogen atom between them forms a four or five-membered ring which is optionally substituted with a hydroxyl group, or a tautomer, pharmaceutically acceptable salt, solvate or amino-protected derivative thereof.

In yet a further embodiment there are provided the following compounds:

N2-(2,3-Dichloro-benzyl)-5-nitro-N4-piperidin-4-ylmethyl-pyridine-2,4-diamine

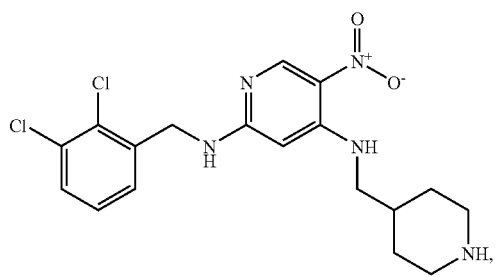

N2-[2-(3-Chloro-phenyl)-ethyl]-5-nitro-N4-piperidin-4-ylmethyl-pyridine-2,4-diamine

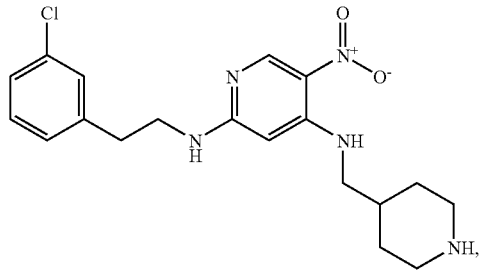

5-Nitro-N2-phenethyl-N4-piperidin-4-ylmethyl-pyridine-2,4-diamine

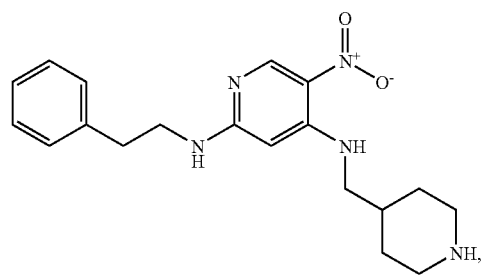

N4-(4-Aminomethyl-cyclohexylmethyl)-5-nitro-N2-(2-trifluoromethoxy-benzyl)-pyridine-2,4-diamine

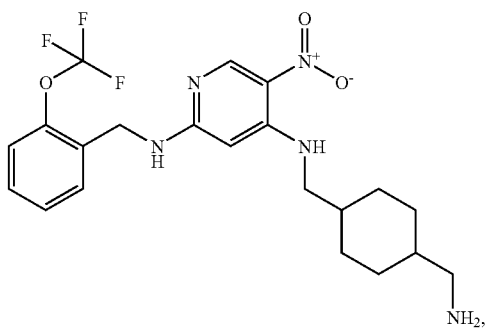

N4-(4-Aminomethyl-cyclohexylmethyl)-N2-(2,3-dichloro-benzyl)-5-nitro-pyridine-2,4-diamine

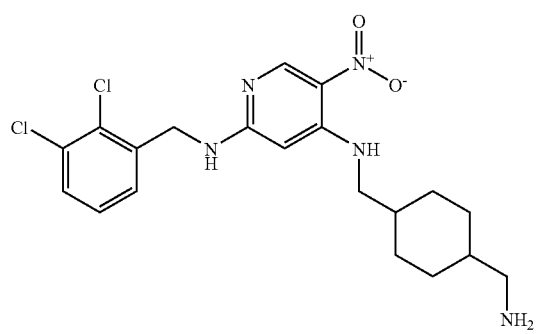

13
N4-(4-Aminomethyl-cyclohexylmethyl)-5-nitro-N2-phenethyl-pyridine-2,4-diamine

14
N4-(4-trans-Aminomethyl-cyclohexylmethyl)-5-nitro-N2-(2-trifluoromethoxy-benzyl)-pyridine-2,4-diamine

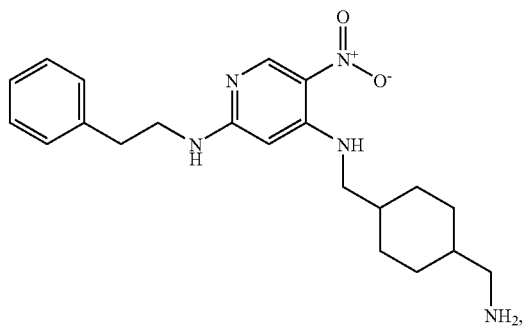

N4-(4-Aminomethyl-cyclohexylmethyl)-N2-[2-(3-chloro-phenyl)-ethyl]-5-nitro-pyridine-2,4-diamine

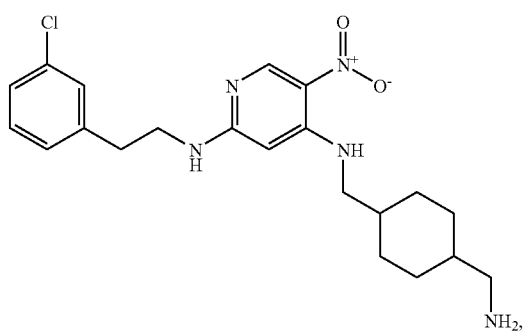

N4-(4-Aminomethyl-cyclohexylmethyl)-5-nitro-N2-(2-chloro-benzyl)-pyridine-2,4-diamine, m/z 404.0 (M+H)⁻

N4-(4-trans-Amino-cyclohexylmethyl)-5-nitro-N2-(2-trifluoromethoxy-benzyl)-pyridine-2,4-diamine

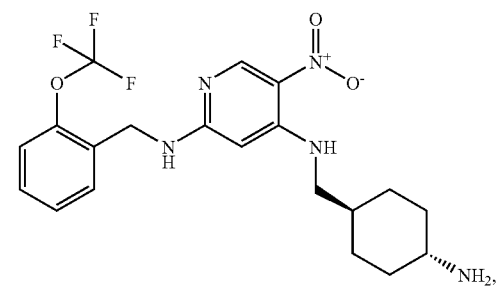

5-nitro-N4-piperidin-4-ylmethyl-N2-(2-trifluoromethoxy-benzyl)-pyridine-2,4-diamine

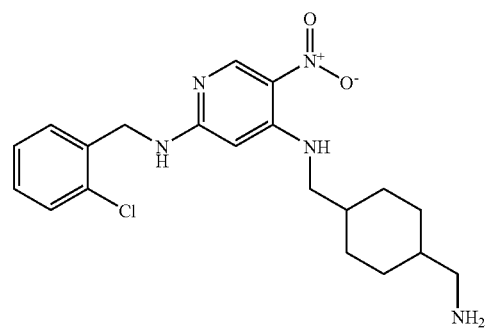

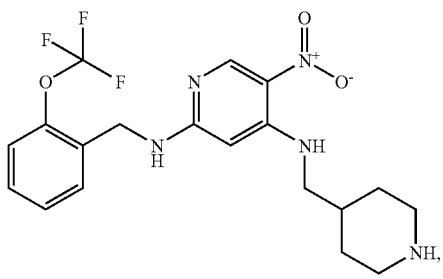

15

4-[(4-aminomethyl-cyclohexylmethyl)-amino]-6-(2-chloro-benzylamino)-nicotinamide

16

5-Nitro-N4-(4-pyrrolidin-1-ylmethyl-cyclohexylmethyl)-N²-(2-trifluoromethoxy-benzyl)-pyridine-2,4-diamine

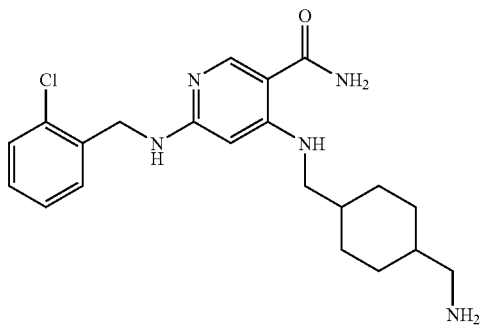

4-[(4-aminomethyl-cyclohexylmethyl)-amino]-6-(2-chloro-benzylamino)-nicotinonitrile

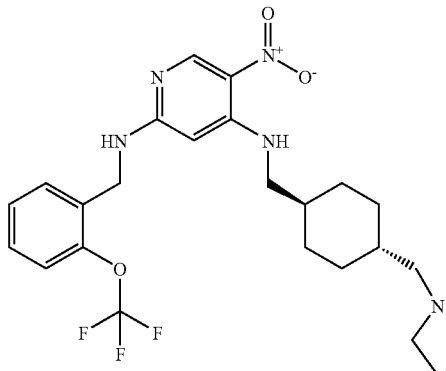

5-Nitro-N⁴-(4-azetidin-1-yl-cyclohexylmethyl)-N²-(2-trifluoromethoxy-benzyl)-pyridine-2,4-diamine

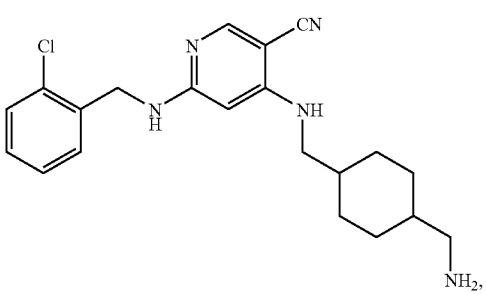

5-Nitro-N⁴-(4-pyrrolidin-1-yl-cyclohexylmethyl)-N²-(2-trifluoromethoxy-benzyl)-pyridine-2,4-diamine

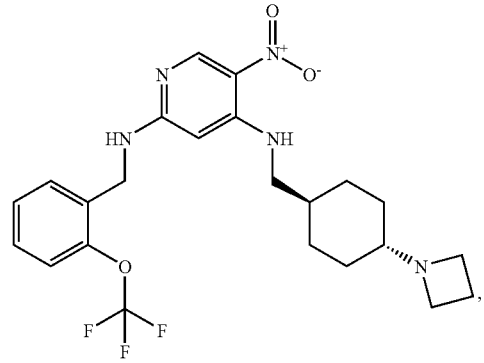

1-(4-{[5-Nitro-2-(2-trifluoromethoxy-benzylamino)-pyridin-4-ylamino]-methyl}-cyclohexyl)-azetidin-3-ol

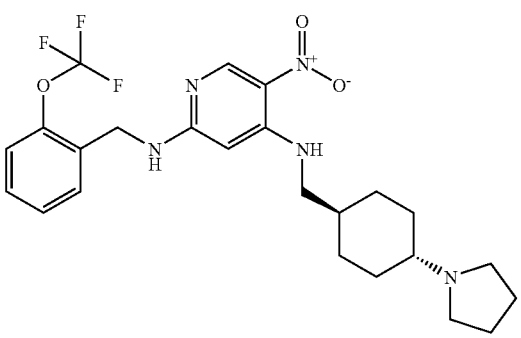

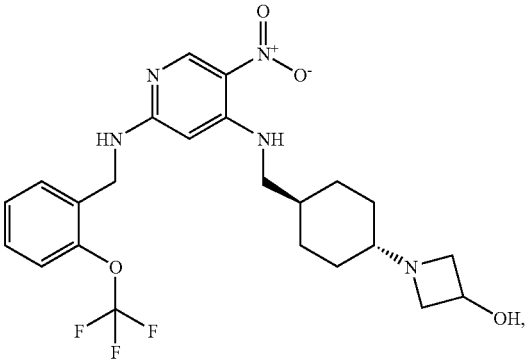

1-(4-{[5-Nitro-2-(2-trifluoromethoxy-benzylamino)-pyridin-4-ylamino]-methyl}-cyclohexylmethyl)-azetidin-3-ol

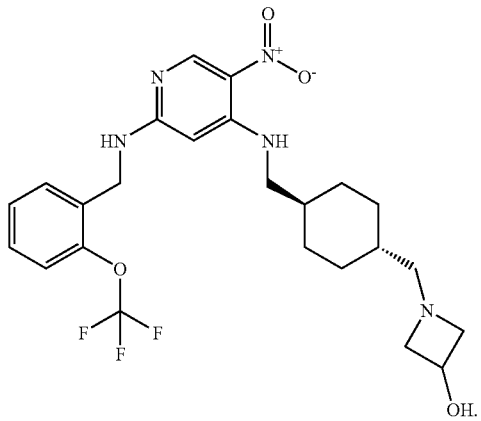

General Synthetic Methods

The compounds of the invention may be prepared by the methods described below. In each of the schemes below, the groups X, Y, $R_1$, $R_2$ and $R_3$ are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art from commercially available materials using methods described in the chemical literature.

Compounds of formula (I) having $YR_3$=NR'R'' may be prepared as illustrated in Scheme I and described below.

Scheme I

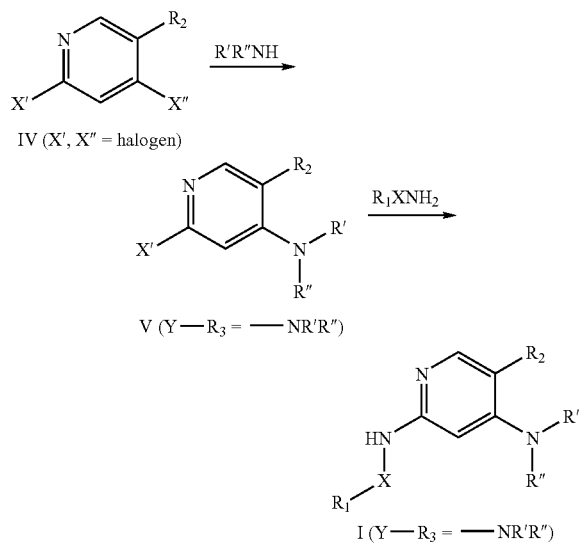

As illustrated above, a 2,4-dihalopyridine (IV), preferably a 2,4-dichloropyridine, is reacted with about one equivalent of an amine (R'R''NH) in the presence of a base, such as diisopropylethylamine, in a suitable solvent, such as EtOH or DMA (dimethylacetamide), to provide intermediate V. The reaction is carried out preferably at about room temperature. Intermediate V is then reacted with a second amine $R_1XNH_2$ in a suitable solvent, such as DMA, to provide the desired I. The reaction is preferably heated to about 100° C.

For compounds of formula (I) where the $R_2$ group is generally less electron withdrawing than $NO_2$, such as $R_2$=CN or $CONH_2$, the compounds may be prepared as illustrated in Scheme II and described below.

Scheme II

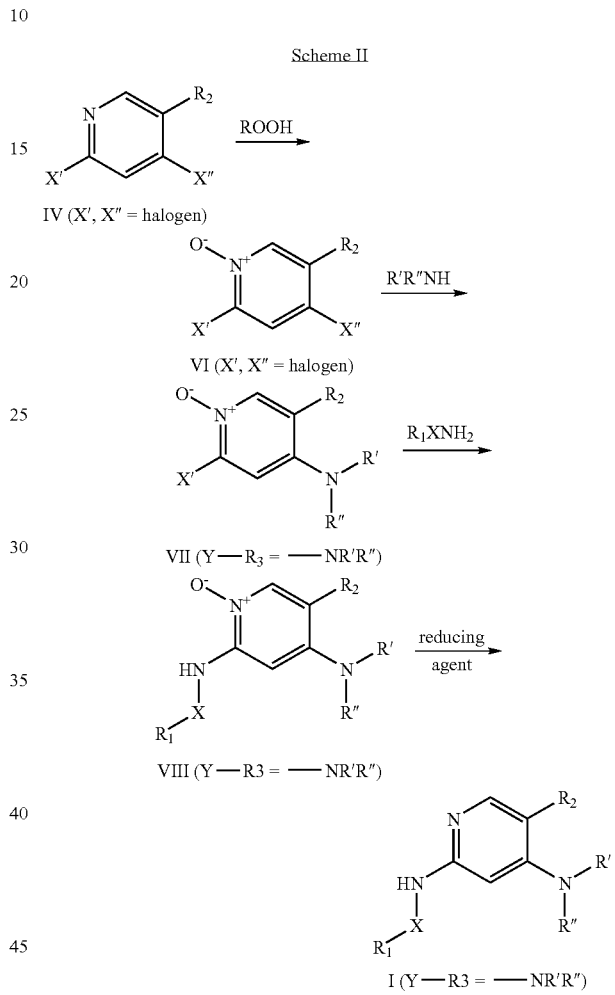

As illustrated above a 2,4-dihalopyridine (IV), preferably 2,4-dichloropyridine, is reacted with an oxidizing agent, such as urea hydrogen peroxide in a suitable solvent, such as acetonitrile, to provide intermediate (VI). The reaction is carried out preferably between about 0° C. and room temperature. Intermediate (VI) is reacted with about one equivalent of an amine (R'R''NH) in the presence of a base, such as diisopropylethylamine, in a suitable solvent, such as EtOH, to provide intermediate (VII). The reaction is carried out preferably at about room temperature to about 60° C. Intermediate (VII) is then reacted with a second amine $R_1XNH_2$ in a suitable solvent, such as dioxane, to provide the intermediate (VIII). The reaction is preferably heated to about 100° C. Intermediate (VIII) is then reacted with a reducing agent, such as zinc powder, in a suitable solvent, such as aqueous ammonium chloride and THF, to provide the desired I. The reaction is preferably carried out at about room temperature. If $R_3$ or $R_1$ contains a second amine group, (i.e., in the R' and/or R'' groups in Scheme I and II above) the second amine is preferably protected with a suitable amino-protecting group, for example with a Boc-group, prior to reaction with intermediate (IV) or (VI), and the amine is deprotected after reaction of the pyridine intermediate (V) with $R_1XNH_2$, or following reduction of intermediate (VIII). For example, in the case of 1-amino-4-aminomethylcyclohexane as illustrated in Scheme III, the mono-Boc-protected diamine is reacted with (IV) as described above. The resulting intermediate (IX) is then reacted with $R_1XNH_2$ as described above, and the Boc-protected intermediate (X) is then deprotected by treatment with acid to provide the desired compound of formula (I). The free amino group is then reacted with suitable reagents, such as alkylating agents or, under reductive conditions, carbonyl compounds, to provide the N-monoalkylated or N-dialkylated product of formula (I).

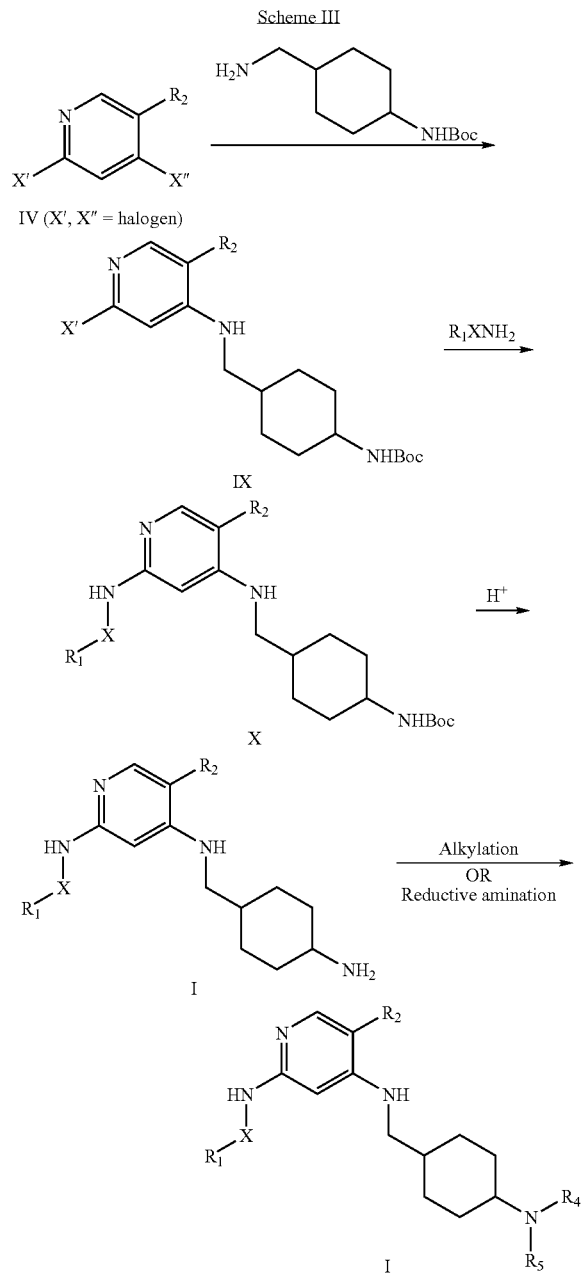

Substituents $R_1$, $R_2$ and $R_3$ may be further modified by methods known in the art to obtain additional compounds of formula (I). Some of these modifications are illustrated in the synthetic examples below.

Compounds of formula (I) having Y=O or S may be prepared using the same general processes of Schemes I to III above, but reacting IV or VI with the desired R'OH or R'SH in the presence of a suitable base such as sodium hydride in a suitable solvent such as THF or DMF, in place of the amine (R'R"NH), to obtain I (Y—$R_3$=—OR' or —SR' respectively).

In order that this invention be more fully understood, the following examples are set forth. These examples are for the purpose of illustrating embodiments of this invention, and are not to be construed as limiting the scope of the invention in any way. Starting materials used are either commercially available or easily prepared from commercially available materials by those skilled in the art.

SYNTHETIC EXAMPLES

Example 1

Synthesis of 2,4-dichloro-5-nitro-pyridine

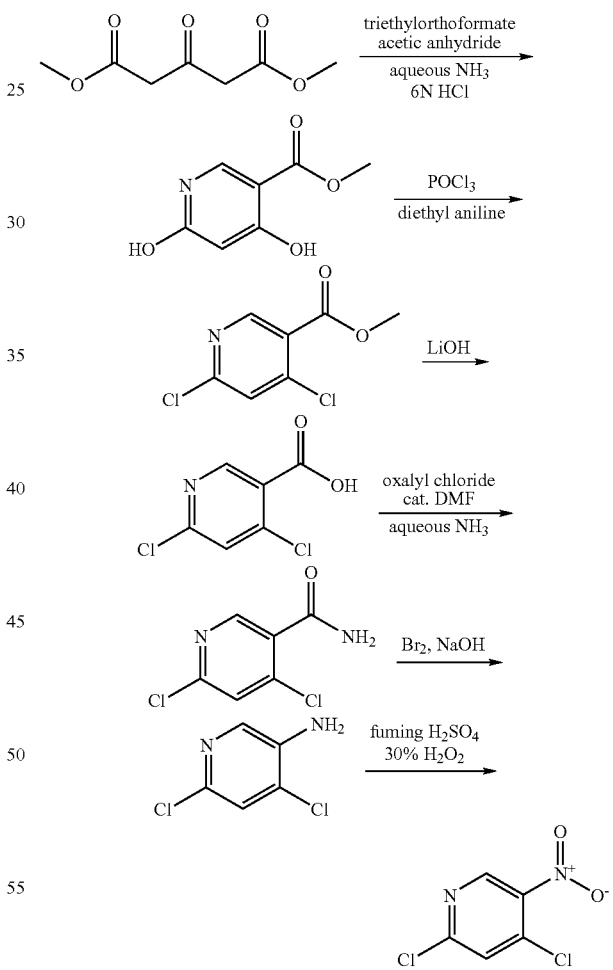

Dimethyl-1,3-acetonedicarboxylate (50.0 g, 287 mmol), triethylorthoformate (47.8 mL, 287 mmole), and acetic anhydride (54.2 mL, 102 mmol) were combined and heated to 130° C. for 1.5 h then allowed to cool to 25° C. The volatiles were removed in vacuo while maintaining the water bath around 85° C. until the volume of the reaction was reduced to about 25 mL. This crude liquid was poured into a 2000 mL flask and cooled in an ice bath. To this cooled flask was added 75 mL of concentrated aqueous NH₃ in portions with swirling. After 1 hour the mixture was acidified by the addition of 6 N HCl (~250 mL). The yellow precipitate was collected by vacuum filtration and allowed to dry under a stream of air. The crude powder was boiled in 200 mL of benzene and allowed to cool and filtered to provide 4,6-dihydroxy-nicotinic acid methyl ester as an orange solid (25.7 g, 53%).

4,6-Dihydroxy-nicotinic acid methyl ester (25.7 g, 152 mmol) was dissolved in POCl₃ (218 mL). Diethyl aniline (36.3 mL, 243.2 mmol) was added and the reaction was fitted with an air cooled condenser and heated to 120° C. for 2 h then allowed to cool to 25° C. over 18 h. The reaction solution was poured slowly and portion-wise over the ice. Following the addition of the complete contents, EtOAc was added and the biphasic mixture was poured into a separatory funnel. The aqueous phase was separated and extracted twice with EtOAc. The organic layers were combined, dried (Na₂SO₄), decanted and concentrated. The resultant orange oil crystallized upon standing to afford 4,6-dichloro-nicotinic acid methyl ester as an orange solid (27.4 g, 88%).

4,6-Dichloro-nicotinic acid methyl ester (27.3 g, 133 mmol) was dissolved in THF (150 mL). LiOH (3.53 g, 147 mmol), dissolved in H₂O (25 mL), was added dropwise and the reaction was allowed to stir for 18 h. The volatiles were removed in vacuo. The resultant residue was diluted with H₂O (100 mL) and acidified with 6 N HCl while swirling at 0° C. The solution was brought to a pH of 2.0 and a yellow precipitate formed. The mixture was allowed to stand at 0° C. for 1 h then filtered to afford 4,6-dichloro-nicotinic acid as a yellow solid (20.6, 81%).

4,6-Dichloro-nicotinic acid (10.3 g, 53.4 mmol) was suspended in CH₂Cl₂ (200 mL). Oxalyl chloride (14 mL, 158 mmol) was added and the reaction was placed in an ice bath. DMF (1.0 mL) was added and the reaction was fitted with an air cooled condenser. The reaction was stirred for 3 h and allowed to warm to 25° C. The volatiles were removed in vacuo and the crude residue was resuspended in THF (200 mL) and cooled to 0° C. To this stirred suspension was added concentrated aqueous ammonia (75 mL) dropwise and the reaction was allowed to stir for 1 h. The volatiles were removed and the crude was redissolved in EtOAc and poured into brine. The aqueous phase was separated and extracted twice with EtOAc. The organic layers were combined, dried (Na₂SO₄), decanted and concentrated to afford 4,6-dichloro-nicotinamide as a beige solid (7.27 g, 71%).

NaOH (6.60 g, 165 mmol) was dissolved in H₂O (31 mL) and cooled in an ice bath. Bromine (2.08 mL, 40.6 mmol) was added dropwise and the yellow solution was stirred for 15 min. 4,6-Dichloro-nicotinamide (7.27 g, 38.1 mmol) in 1,4-dioxane (21 mL) was added dropwise to the bromine solution over 30 min. The reaction was allowed to warm slowly to 25° C. over 18 h. The volatiles were removed in vacuo and the resultant solution was diluted with brine and poured into EtOAc. The aqueous phase was separated and extracted twice with EtOAc. The organic layers were combined, dried (Na₂SO₄), decanted and concentrated to afford an orange oil. The resultant oil was purified on a 100 g SiO₂ flash chromatography cartridge with 25 % EtOAc-hexanes to afford 4,6-dichloro-pyridin-3-ylamine as a tan solid (4.54 g, 73%).

30% Aqueous H₂O₂ solution (29 mL) was cooled in an ice bath. Fuming H₂SO₄ (13 mL) was added dropwise to the stirred vessel. In a separate flask, concentrated H₂SO₄ was added to 4,6-dichloro-pyridin-3-ylamine (4.54 g, 27.9 mmol) and stirred until complete dissolution occurred. The amine solution was then added to the H₂O₂/fuming H₂SO₄ solution, dropwise. The reaction was allowed to warm to 25° C. over 18 h. The yellow solution was poured over ice and neutralized by the slow addition of solid NaHCO₃. The resultant aqueous solution was extracted three times with EtOAc and the combined organic layers were dried (Na₂SO₄), decanted and concentrated to afford 2,4-dichloro-5-nitro-pyridine as a yellow solid (4.13 g, 77%).

Example 2

Synthesis of 5-nitro-$N^4$-piperidin-4-ylmethyl-$N^2$-(2-trifluoromethoxy-benzyl)-pyridine-2,4-diamine

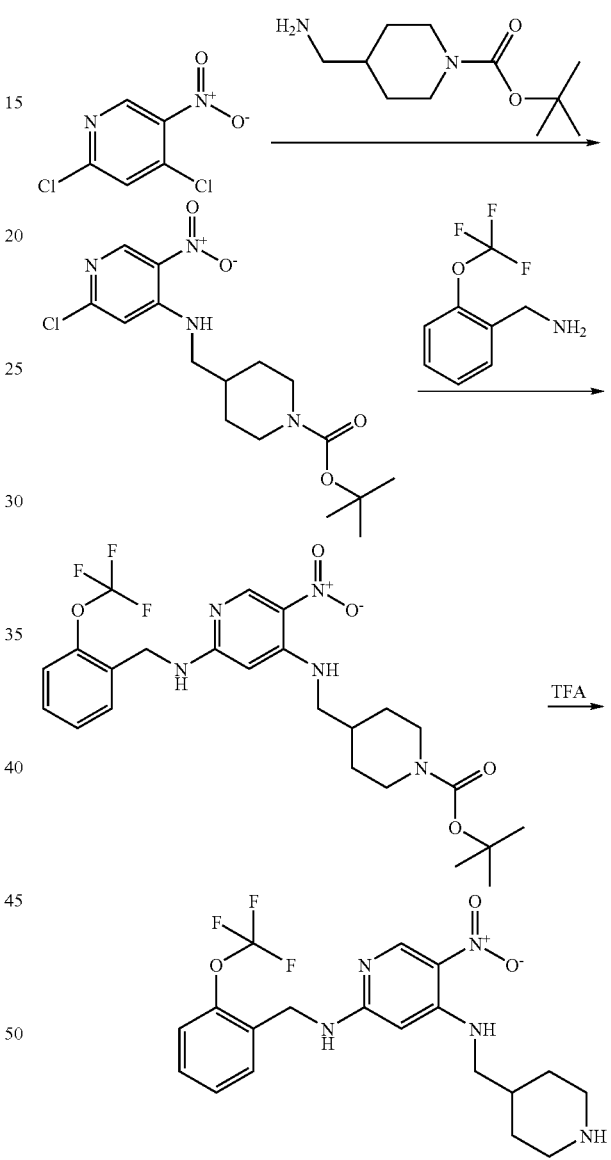

2,4-Dichloro-5-nitro-pyridine (500 mg, 2.59 mmol) was dissolved in EtOH-DMA (15 mL, 1:1). To this solution was added diisopropylethyl amine (0.99 mL, 5.7 mmol) followed by 4-aminomethyl-piperidine-1-carboxylic acid tert-butyl ester (611 mg, 2.85 mmol). The reaction was stirred for 18 h, then concentrated in vacuo. The crude residue was rediluted in EtOAc and poured into H₂O. The aqueous phase was separated and extracted two more times with EtOAc. The organic layers were combined, dried (Na₂SO₄), decanted and concentrated. The crude residue was purified by SiO₂ flash chromatography eluting with 2% CH₃OH—CH₂Cl₂ to afford 4-[(2-chloro-5-nitro-pyridin-4-ylamino)-methyl]-piperidine-1-carboxylic acid tert-butyl ester as a yellow foam (780 mg, 81%).

The 4-[(2-chloro-5-nitro-pyridin-4-ylamino)-piperidine-1-carboxylic acid tert-butyl ester (100 mg, 0.27 mmol) was dissolved in DMA (5.0 mL). 2-Trifluoromethoxy-benzyl amine (153 mg, 0.80 mmol) was added followed by diisopropylethylamine (0. 14 mL, 0.80 mmol). The reaction was heated to 100° C. and stirred for 18 h, then cooled to 25° C. The volatiles were removed in vacuo and the crude product was purified by flash column chromatography (SiO$_2$, 15-50% EtOAc-hexanes) to afford 4-{[5-nitro-2-(2-trifluoromethoxy-benzylamino)-pyridin-4-ylamino]-methyl}-piperidine-1-carboxylic acid tert-butyl ester as a yellow foam (91 mg, 64%).

4-{[5-Nitro-2-(2-trifluoromethoxy-benzylamino)-pyridin-4-ylamino]-methyl}-piperidine-1-carboxylic acid tert-butyl ester (91 mg, 0.17 mmol) was dissolved in CH$_2$Cl$_2$ (2.5 mL). TFA (2.5 mL) was added and the reaction was stirred for 3 h. The volatiles were removed and the resultant residue was redissolved in EtOAc and poured into 10% aqueous NaHCO$_3$. The aqueous phase was separated and extracted two more times with EtOAc. The organic layers were combined, dried (Na$_2$SO$_4$), decanted and concentrated. The crude product was purified by SiO$_2$ chromatography (1:10:89, NH$_4$OH:CH$_3$OH:CH$_2$Cl$_2$) to afford 5-nitro-N$^4$-piperidin-4-ylmethyl-N$^2$-(2-trifluoromethoxy-benzyl)-pyridine-2,4-diamine as a yellow solid, m/z 426.4 (M+H)$^+$ (28 mg, 39%).

The following compounds were prepared by methods analogous to those described in Example 2.

N2-(2,3-Dichloro-benzyl)-5-nitro-N4-piperidin-4-ylmethyl-pyridine-2,4-diamine, m/z 410.3 (M+H)

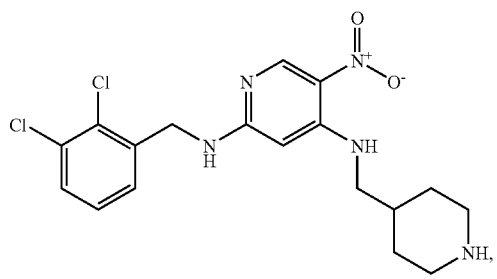

N2-[2-(3-Chloro-phenyl)-ethyl]-5-nitro-N4-piperidin-4-ylmethyl-pyridine-2,4-diamine, m/z 390.4 (M+H)$^+$

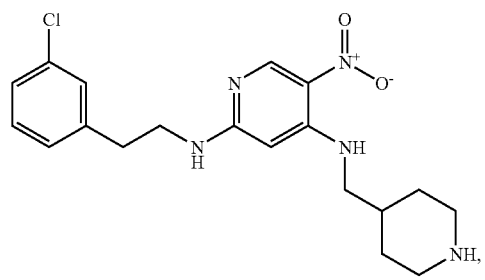

5-Nitro-N2-phenethyl-N4-piperidin-4-ylmethyl-pyridine-2,4-diamine, m/z 356.6 (M+H)$^+$

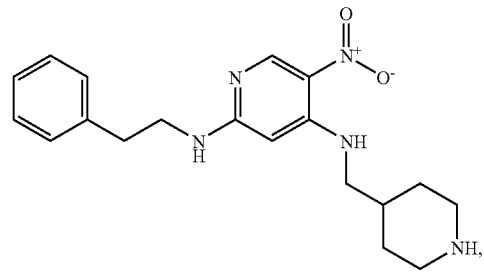

N4-(4-Aminomethyl-cyclohexylmethyl)-5-nitro-N2-(2-trifluoromethoxy-benzyl)-pyridine-2,4-diamine, m/z 454.5 (M+H)$^+$

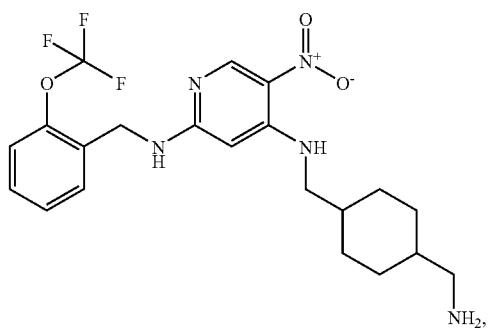

N4-(4-Aminomethyl-cyclohexylmethyl)-N2-(2,3-dichloro-benzyl)-5-nitro-pyridine-2,4-diamine, m/z 438.4 (M+H)$^-$

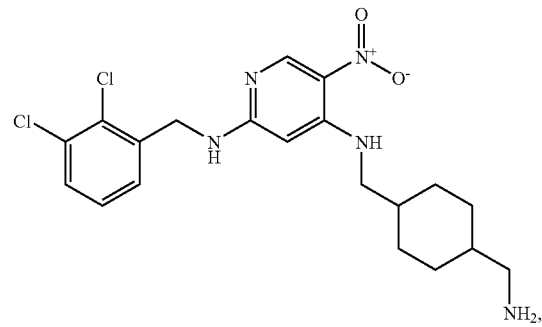

25

N4-(4-Aminomethyl-cyclohexylmethyl)-5-nitro-N2-phenethyl-pyridine-2,4-diamine, m/z 384.5 (M+H)+

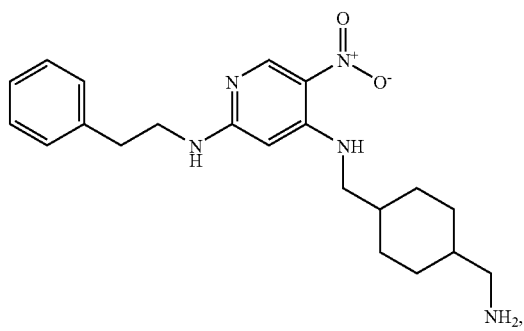

N4-(4-Aminomethyl-cyclohexylmethyl)-N2-[2-(3-chloro-phenyl)-ethyl]-5-nitro-pyridine-2,4-diamine, m/z 418.3 (M+H)+

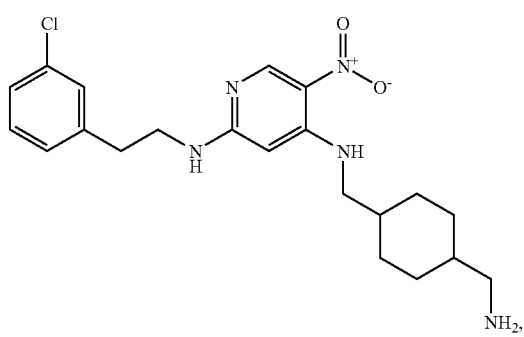

N4-(4-Aminomethyl-cyclohexylmethyl)-5-nitro-N2-(2-chloro-benzyl)-pyridine-2,4-diamine, m/z 404.0 (M+H)+

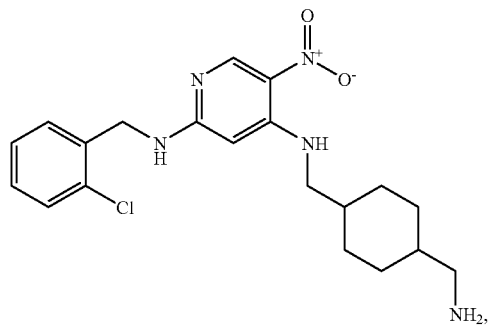

26

N4-(4-trans-Aminomethyl-cyclohexylmethyl)-5-nitro-N2-(2-trifluoromethoxy-benzyl)-pyridine-2,4-diamine, m/z 454.6 (M+H)+

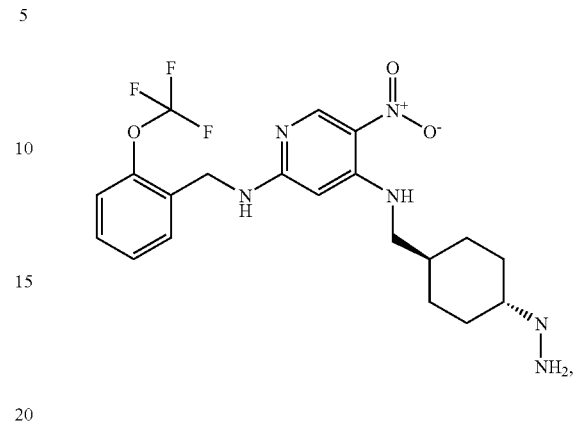

N4-(4-trans-Amino-cyclohexylmethyl)-5-nitro-N2-(2-trifluoromethoxy-benzyl)-pyridine-2,4-diamine, m/z 440.5 (M+H)+

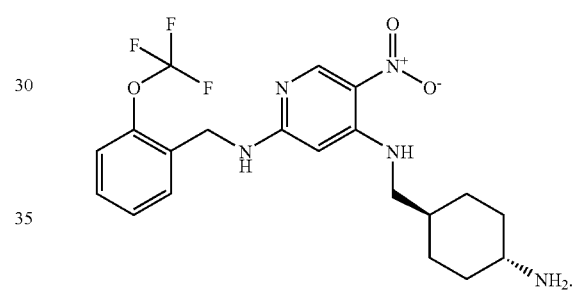

Example 3

Synthesis of 4-[(4-aminomethyl-cyclohexylmethyl)-amino]-6-(2-chloro-benzylamino)-nicotinamide

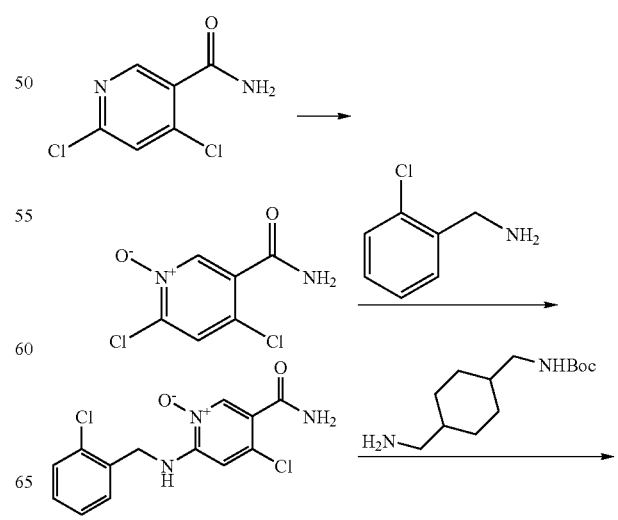

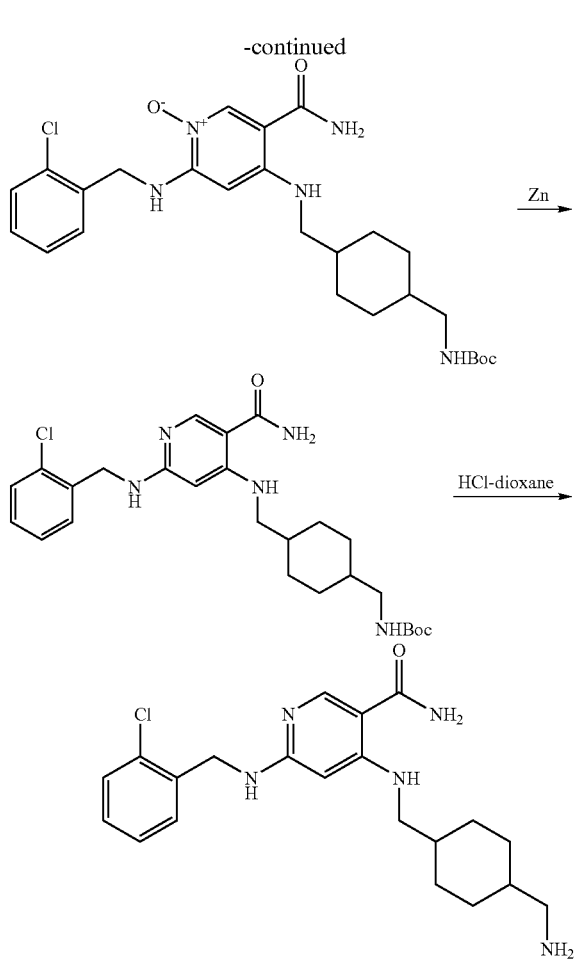

A mixture of (4-{[5-carbamoyl-2-(2-chloro-benzylamino)-1-oxy-pyridin-4-ylamino]-methyl}-cyclohexylmethyl)-carbamic acid tert-butyl ester (88 mg, 0.17 mmol), zinc powder (190 mg, 2.90 mmol), 30% aqueous $NH_4Cl$ (8 mL), and THF (8 mL) was stirred at ambient temperature for 24 h. The mixture was extracted with $CH_2Cl_2$ (2×30 mL) and the combined organic layers were dried over $Na_2SO_4$ before concentrating in vacuo. The residue was purified by silica-gel column chromatography ($CH_2Cl_2/CH_3OH$, 20:1 v/v) to afford (4-{[5-carbamoyl-2-(2-chloro-benzylamino)-pyridin-4-ylamino]-methyl}-cyclohexylmethyl)-carbamic acid tert-butyl ester as a white solid (60 mg, 70%).

A mixture of (4-{[5-carbamoyl-2-(2-chloro-benzylamino)-pyridin-4-ylamino]-methyl}-cyclohexylmethyl)-carbamic acid tert-butyl ester (40 mg, 0.080 mmol), 4 N HCl-dioxane (2 mL) and MeOH (0.5 mL) was stirred at ambient temperature for 24 h. Volatiles were evaporated in vacuo and the residue was purified by semi-preparative HPLC ($CH_3CN/H_2O$/0.05% TFA) to afford the TFA salt of 4-[(4-aminomethyl-cyclohexylmethyl)-amino]-6-(2-chloro-benzylamino)-nicotinamide as a white solid (20 mg, 40%), m/z 402 $(M+H)^+$.

Example 4

Synthesis of 4-[(4-aminomethyl-cyclohexylmethyl)-amino]-6-(2-chloro-benzylamino)-nicotinonitrile

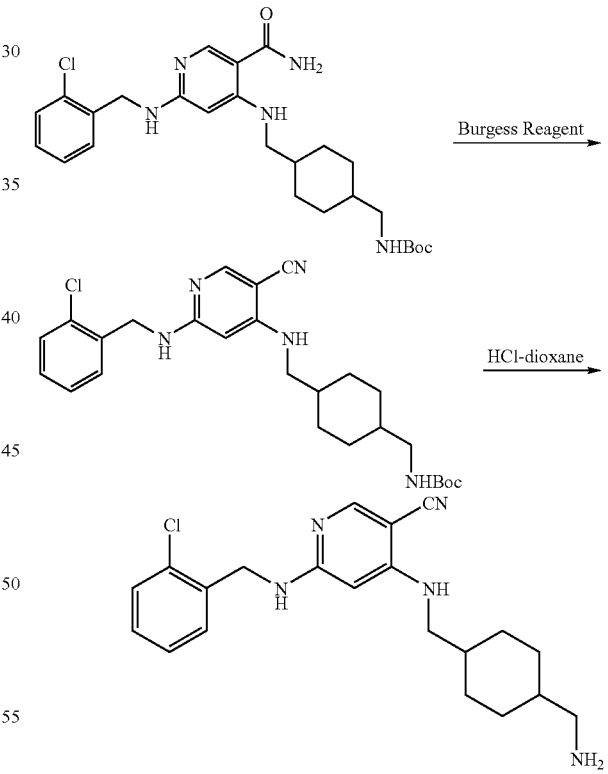

To a suspension of 4,6-dichloro-nicotinamide (1.94 g, 10.26 mmol) in acetonitrile (20 mL) at ambient temperature, was added urea hydrogen peroxide (UHP) (2.90 g, 30.80 mmol). The mixture was cooled to 0° C. before trifluoroacetic anhydride (2.85 mL, 20.52 mmol) was added. The resulting mixture was allowed to warm up to ambient temperature and stirred for 3 h. 4,6-Dichloro-1-oxy-nicotinamide was obtained by filtration of the reaction mixture and was combined with another portion isolated by purifying the residual filtrate by silica gel column chromatography (EtOAc then $CH_2Cl_2$/MeOH, 20:1 v/v). The two batches were combined to afford the product (1.30 g, 62%).

To a mixture of 4,6-dichloro-1-oxy-nicotinamide (600 mg, 2.91 mmol), 2-chlorobenzylamine (412 mg, 2.91 mmol) and EtOH (2 mL) was added diisopropylethylamine (0.61 mL, 3.5 mmol). The mixture was stirred at ambient temperature for 18 h then heated to 60° C. for 4 h. 4-Chloro-6-(2-chloro-benzylamino)-1-oxy-nicotinamide was obtained as an off-white solid by filtration of the reaction mixture (296 mg, 33%).

A mixture of 4-chloro-6-(2-chloro-benzylamino)-1-oxy-nicotinamide (135 mg, 0.42 mmol), (4-aminomethyl-cyclohexylmethyl)-carbamic acid tert-butyl ester (203 mg, 0.87 mmol), diisopropylethylamine (82 μL, 0.47 mmol) and dioxane (2 mL) was refluxed for 2 days. (4-{[5-Carbamoyl-2-(2-chloro-benzylamino)-1-oxy-pyridin-4-ylamino]-methyl}-cyclohexylmethyl)-carbamic acid tert-butyl ester was obtained as an off-white solid by filtration of the reaction mixture. The filtrate was concentrated and purified by silica-gel column chromatography ($CH_2Cl_2$/MeOH, 20:1 to 10:1 v/v) to afford additional product. The two batches were combined to afford the product (160 mg, 73%).

To a suspension of (4-{[5-carbamoyl-2-(2-chloro-benzylamino)-pyridin-4-ylamino]-methyl}-cyclohexylmethyl)-carbamic acid tert-butyl ester (31 mg, 0.062 mmol) in $CH_2Cl_2$ at ambient temperature was added Burgess reagent (40 mg, 0.168 mmol) in portions over 3 h. The resultant mixture was stirred at 25° C. for another 1 h and then water was added. The mixture was stirred for 20 min and extracted with $CH_2Cl_2$ (2×15 mL). The combined organic layers were dried over $Na_2SO_4$ and concentrated in vacuo. The residue was purified by silica-gel column chromatography (hexanes/EtOAc, 2:1 v/v then EtOAc) to afford (4-{[2-(2-chloro-benzylamino)-5-cyano-pyridin-4-ylamino]-methyl}-cyclohexylmethyl)-carbamic acid tert-butyl ester as a white solid (12 mg, 40%).

A mixture of (4-{[2-(2-chloro-benzylamino)-5-cyano-pyridin-4-ylamino]-methyl}-cyclohexylmethyl)-carbamic acid tert-butyl ester (12 mg, 0.025 mmol) and 4 N HCl/dioxane (3 mL) was stirred at ambient temperature for 18 h. Evaporation of the volatiles in vacuo afforded the HCl salt of 4-[(4-aminomethyl-cyclohexylmethyl)-amino]-6-(2-chloro-benzylamino)-nicotinonitrile as a white solid (11 mg, 100%), m/z 384 (M+H)$^+$.

Example 5

5-Nitro-N$^4$-(4-pyrrolidin-1-yl-cyclohexylmethyl)-N$^2$-(2-trifluoromethoxy-benzyl)-pyridine-2,4-diamine

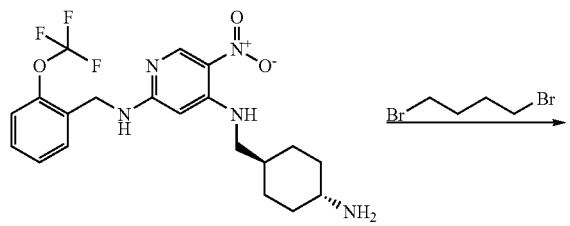

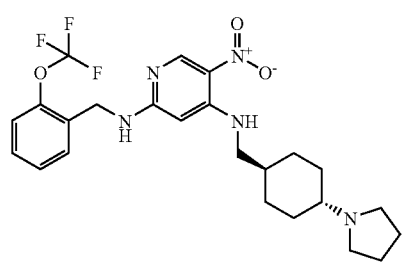

N4-(4-trans-Amino-cyclohexylmethyl)-5-nitro-N2-(2-trifluoromethoxy-benzyl)-pyridine-2,4-diamine (70 mg, 0.16 mmol) was dissolved in DMA (3 mL). To this solution was added 1,4-dibromobutane (95 □L, 0.80 mmol) and Na$_2$CO$_3$ (85 mg, 0.80 mmol). The reaction was heated in a Personal Chemistry Microwave Reactor at 100° C. for 10 min. The heating for 10 minutes was repeated 3 times. The volatiles were removed and the reaction was diluted with EtOAc and poured into H$_2$O. The aqueous phase was separated and extracted two more times with EtOAc. The organic layers were combined, dried (Na$_2$SO$_4$), decanted and concentrated. The crude residue was purified on a preparative TLC plate (SiO$_2$, 1000 micron thickness) eluting with NH$_4$OH:CH$_3$OH:CH$_2$Cl$_2$ (1:10:89) to afford the title compound as a pale yellow foam (36 mg, 48%), m/z 494.7 (M+H)$^+$.

The following compound was prepared by methods analogous to those described in Example 5:

5-Nitro-N$^4$-(4-pyrrolidin-1-ylmethyl-cyclohexylmethyl)-N$^2$-(2-trifluoromethoxy-benzyl)-pyridine-2,4-diamine, m/z 508.7 (M+H)$^+$

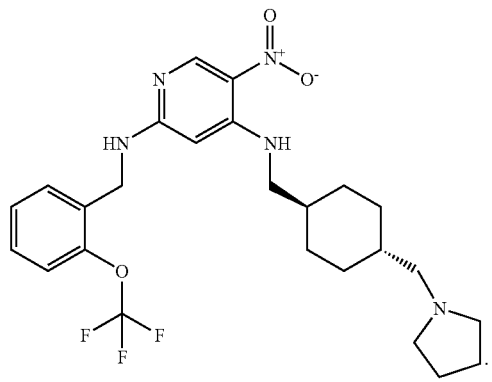

The following compound was prepared by methods analogous to those described in Example 5, substituting 1,3-dibromopropane for 1,4-dibromobutane:

5-Nitro-A4-(4-azetidin-1-yl-cyclohexylmethyl)-N$^2$-(2-trifluoromethoxy-benzyl)-pyridine-2,4-diamine, m/z 480.7 (M+H)$^+$

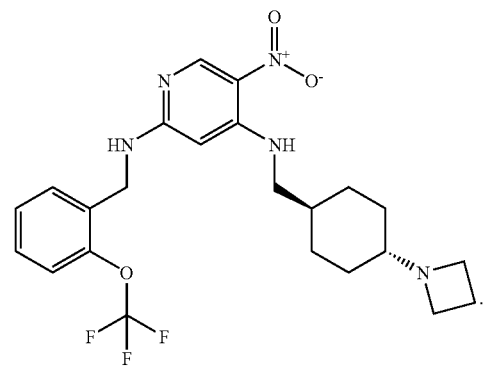

The following compounds were prepared by methods analogous to those described in Example 5, substituting 1,3-dibromo-2-propanol for 1,4-dibromobutane:

1-(4-{[5-Nitro-2-(2-trifluoromethoxy-benzylamino)-pyridin-4-ylamino]-methyl}-cyclohexyl)-azetidin-3-ol, m/z 496.7 (M+H)$^+$

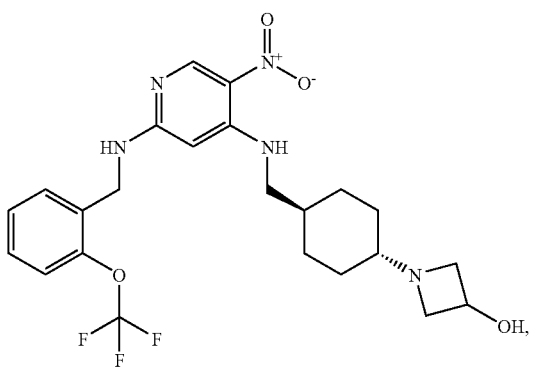

1-(4-{[5-Nitro-2-(2-trifluoromethoxy-benzylamino)-pyridin-4-ylamino]-methyl}-cyclohexylmethyl)-azetidin-3-ol, m/z 510.8 (M+H)+

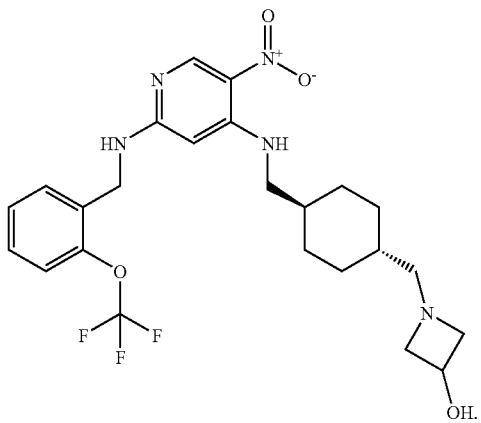

Assessment of Biological Activity

PKC-theta Inhibition Assay

The ability of compounds to inhibit the kinase activity of PKC-theta was measured using a firefly-luciferase reagent (PKLight™—Cambrex #LT07).

Compounds are diluted in 100% DMSO at 100× the final desired assay concentration. Compounds are subsequently diluted 1:25 into complete assay buffer (50 mM HEPES/KOH, pH 7.5; 10 mM MgCl$_2$; 50 mM KCl; 0.01% CHAPS; 0.1% BSA; 200 μM TCEP). 25 μl of the 4× in 4% DMSO stocks are transferred to 384-well white polystyrene plates (Greiner #781075). 25 μl of a mixture containing 20 μM peptide substrate and 4 μM ATP are added to the compounds; followed by 50 μl of 4 nM PKC-theta. Blank wells are defined by the addition of an equal volume of assay buffer in place of the PKC-theta.

Final assay concentrations are as follows: 2 nM PKC-theta, 5 μM peptide substrate, 1 μM ATP. The complete reaction is allowed to incubate at room temperature for 90-120 minutes. Following this incubation period the reaction is terminated by the addition of 100 μl of the PKLight™ reagent. This reaction is allowed to incubate for 15 minutes after which luminescence is quantified using an LJL Analyst.

The compounds in the synthetic examples above that were evaluated in the firefly-luciferase PKC-theta assay above were found to have IC$_{50}$'s less than 1 microM; preferred compounds had IC$_{50}$'s equal to or less than 0.035 microM.

Some of the compounds in the synthetic examples above were also tested against Syk, Lyn, Veg-f and insulin receptor kinase to evaluate selectivity for PKC-theta inhibition. Some compounds were also tested against other kinases including CDK-2 and PLK. Many of the compounds demonstrated selectivity for the inhibition of PKC-theta as compared to one or more of the other kinases tested.

Assay conditions for testing against other kinases are generally known in the art. Examples of suitable assays that can be used are described below:

SYK Kinase Assay

Syk is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly Glu4: Tyr1 (PGTYR).

The kinase assay is performed in kinase assay buffer (50 mM HEPES, pH 7.0, 25 mM MgCl$_2$, 5 mM MnCl$_2$, 50 mM KCl, 100 μM Na3VO4, 0.2% BSA, 0.01% CHAPS, 200 pM TCEP). Test compounds initially dissolved in DMSO at 5 mg/mL, are pre-diluted for dose response (starting conc. 10 μM (or 5 μg/mL), 1 to 3 serial dilutions, 10 doses) with the assay buffer in 96-well polypropylene microtiter plates. A 40 μL volume of diluted enzyme (0.5 nM final conc.) in kinase buffer and a 20 μL aliquot of diluted compound are sequentially added to neutravidin coated 96-well white plate (PIERCE). The kinase reaction is started with a 40 μL volume of a mixture of substrates containing 0.75 μM ATP plus 4.5 ng/μL PGTYR-biotin (CIS Biointernational) in kinase buffer. Background wells are incubated with kinase plus buffer, and the reference inhibitor wells are incubated with 20 μL of 25 μM ADP instead of the compound. The assay plates are incubated for 30 min at room temperature. Following incubation, the assay plates are washed three times with 250 μL wash buffer (50 mM Tris-HCL, pH 7.4, 150 mM NaCl, 0.05% Tween 20, 0.2% BSA). A 100 μL aliquot of europium-labeled anti-phosphotyrosine (Eu3±PT66, Wallac CR04-100) diluted in 50 mM Tris-HCl, pH 7.8, 150 mM NaCl, 10 μM DTPA, 0.05% Tween 40, 0.2% BSA, 0.05% BGG (1 nM final conc.) is added to each well and incubated for 30 min at room temperature. Upon completion of the incubation, the plate is washed four times with 250 μL of wash buffer and 100 μL of DELFIA Enhancement Solution (Wallac) is added to each well. After 15 min or longer, time-resolved fluorescence is measured on the LJL's Analyst (excitation at 360 nm, emission at 620 nm, EU 400 Dichroic Mirror) after a delay time of 250 μs.

LYN Kinase Assay

Lyn(Kd) is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly Glu4: Tyr1 (PGTYR).

The kinase assay is performed in kinase assay buffer (50 mM HEPES, pH 7.0, 25 mM MgCl$_2$, 5 mM MnCl$_2$, 50 mM KCl, 100 μM Na$_3$VO$_4$, 0.2% BSA, 0.01% CHAPS, 200 μM TCEP). Test compounds initially dissolved in DMSO at 5 mg/mL, are pre-diluted for dose response (starting conc. 10 μM (or 5 μg/mL), 1 to 3 serial dilutions, 10 doses) with the assay buffer in 96-well polypropylene microtiter plates. A 40 μL volume of diluted enzyme (0.7 nM final conc.) in kinase buffer and a 20 μL aliquot of diluted compound are sequentially added to neutravidin coated 96-well white plate (PIERCE). The kinase reaction is started with a 40 μL volume of a mixture of substrates containing 1.25 μM ATP plus 4.5 ng/μL PGTYR-biotin (CIS Biointernational) in kinase buffer. Background wells are incubated with kinase plus buffer, and the reference inhibitor wells are incubated with 20 μL of 25 μM ADP instead of the compound. The assay plates are incubated for 30 min at room temperature. Following incubation, the assay plates are washed three times with 250 μL wash buffer (50 mM Tris-HCL, pH 7.4, 150 mM NaCl, 0.05% Tween 20, 0.2% BSA). A 100 μL aliquot of europium-labeled anti-phosphotyrosine (Eu3±PT66, Wallac CR04-100) diluted in 50 mM Tris-HCl, pH 7.8, 150 mM NaCl, 10 μM DTPA, 0.05% Tween 40, 0.2% BSA, 0.05% BGG (1 nM final conc.) is added to each well and incubated for 30 min at room temperature. Upon completion of the incubation, the plate is washed four times with 250 μL of wash buffer and 100 μL of DELFIA Enhancement Solution (Wallac) is added to each well. After 15 min or longer, time-resolved fluorescence is measured on the LJL's Analyst (excitation at 360 nm, emission at 620 nm, EU 400 Dichroic Mirror) after a delay time of 250 μs.

Methods of Therapeutic Use

The compounds of the invention are effective inhibitors of PKC-theta activity, and therefore are useful to inhibit PKC-theta activity in a patient and treat a variety of diseases and disorders that are mediated or sustained through the activity of PKC-theta.

Without wishing to be bound by theory, the compounds of this invention would be expected to inhibit T cell activation via effective inhibition of PKC-theta, and are therefore useful to treat diseases and disorders associated with T cell activation. For example, the inhibition of T cell activation is therapeutically useful for selectively suppressing the immune function. Thus, the inhibition of PKC-theta with the compounds of this invention is an attractive means for treating a variety of immunological disorders, including inflammatory diseases, autoimmune diseases, organ and bone marrow transplant rejection and other disorders associated with T cell mediated immune response. In particular, the compounds of the invention may be used to treat acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with T cell-mediated immune responses will be evident to those of ordinary skill in the art and can also be treated with the compounds and compositions of this invention.

In addition, PKC theta activation has been shown to be associated with insulin resistance in skeletal muscle. Therefore, the inhibition of PKC-theta with the compounds of this invention is also an attractive means for treating type II diabetes.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The invention claimed is:

1. A compound having the following formula (I):

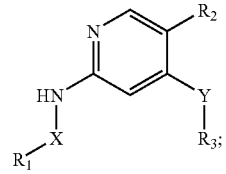

wherein:

X is a bond or $C_{1-6}$alkyl, and wherein the $C_{1-6}$alkyl group is optionally and independently substituted with:
  (A) oxo,
  (B) $C_{1-6}$alkyl which is optionally substituted with one or more of the following groups:
    (i) hydroxyl,
    (ii) $C_{1-6}$alkyloxy,
    (iii) $C_{1-6}$alkylthio,
    (iv) halogen,
  (C) —$COR_6$, wherein $R_6$ is:
    (i) $C_{1-6}$alkyl,
    (ii) $C_{1-6}$alkyloxy,
    (iii) —$NR_7R_8$, wherein $R_7$ and $R_8$ are each independently selected from:
      (a) hydrogen,
      (b) $C_{1-6}$alkyl,
      (c) aryl,
      (d) heteroaryl,
      (e) or wherein $R_7$ and $R_8$ together constitute a methylene bridge which together with the nitrogen atom between them forms a four to six-membered ring, wherein one of the methylene groups is optionally replaced by an oxygen, sulfur or NR group, wherein R is hydrogen or $C_{1-6}$alkyl;
  (D) —OH,
  (E) halogen,
  (F) —$NR_9R_{10}$, wherein $R_9$ and $R_{10}$ are each independently selected from:
    (i) hydrogen,
    (ii) $C_{1-6}$alkyl, optionally substituted with $C_{1-6}$alkyloxy,
    (iii) $C_{1-6}$alkylcarbonyl,
    (iv) $C_{1-6}$alkylsulfonyl,
    (v) aryl,
    (vi) heteroaryl,
    (vii) or wherein $R_9$ and $R_{10}$ together constitute a methylene bridge which together with the nitrogen atom between them forms a four to six-membered ring, wherein one of the methylene groups is optionally replaced by an oxygen, sulfur or NR group, wherein R is hydrogen or $C_{1-6}$alkyl;

Y is —NH—, —O— or —S—;

$R_1$ is a $C_{3-6}$cycloalkyl, aryl or heteroaryl, each of which is optionally and independently substituted with one or more of the following groups:
- (A) $C_{1-6}$alkyl, which is optionally substituted with one or more of the following groups:
  - (i) halogen,
  - (ii) hydroxyl,
  - (iii) amino, which is optionally substituted with $C_{1-6}$alkyl,
- (B) $C_{1-6}$alkyloxy, which is optionally substituted with halogen,
- (C) $C_{1-6}$alkylthio, which is optionally substituted with halogen,
- (D) $C_{1-6}$alkylsulfonyl,
- (E) cyano,
- (F) halogen,
- (G) hydroxyl,
- (H) nitro,
- (I) —$NR_{11}R_{12}$, wherein $R_{11}$ and $R_{12}$ are each independently selected from:
  - (i) hydrogen,
  - (ii) $C_{1-6}$alkyl,
  - (iii) $C_{1-6}$alkylcarbonyl,
  - (iv) $C_{1-6}$alkylsulfonyl,
  - (v) or wherein $R_{11}$ and $R_{12}$ together constitute a methylene bridge which together with the nitrogen atom between them forms a four to six-membered ring, wherein one of the methylene groups is optionally replaced by an oxygen, sulfur or NR group, wherein R is hydrogen or $C_{1-6}$alkyl;
- (J) —$COR_{13}$, wherein $R_{13}$ is:
  - (i) $C_{1-6}$alkyl
  - (ii) $C_{1-6}$alkyloxy,
  - (iii) —OH,
  - (iv) —$NR_{14}R_{15}$, wherein $R_{14}$ and $R_{15}$ are each independently selected from:
    - (a) hydrogen,
    - (b) $C_{1-6}$alkyl,
    - (c) or wherein $R_{14}$ and $R_{15}$ together constitute a methylene bridge which together with the nitrogen atom between them forms a four to six-membered ring, wherein one of the methylene groups is optionally replaced by an oxygen, sulfur or NR group, wherein R is hydrogen or $C_{1-6}$alkyl;
- (K) —O—$R_{16}$, —S—$R_{16}$, or —$SO_2$—$R_{16}$, wherein $R_{16}$ is aryl or heteroaryl optionally and independently substituted with one or more of the following groups:
  - (i) $C_{1-6}$alkyl,
  - (ii) $C_{1-6}$alkyloxy,
  - (iii) —OH,
  - (iv) —$NR_{17}R_{18}$, wherein $R_{17}$ and $R_{18}$ are each independently selected from:
    - (a) hydrogen,
    - (b) $C_{1-6}$alkyl,
    - (c) $C_{1-6}$alkylcarbonyl,
    - (d) $C_{1-6}$alkylsulfonyl,
  - (v) $C_{1-6}$alkylthio,
  - (vi) $C_{1-6}$alkylcarbonyl,
  - (vii) $C_{1-6}$alkylsulfonyl,
  - (viii) cyano,
  - (ix) halogen,
  - (x) nitro;

$R_2$ is selected from the following groups:
- (G) —$CF_3$,
- (H) cyano,
- (I) —$CONH_2$,
- (J) halogen, or
- (K) nitro;

$R_3$ is:

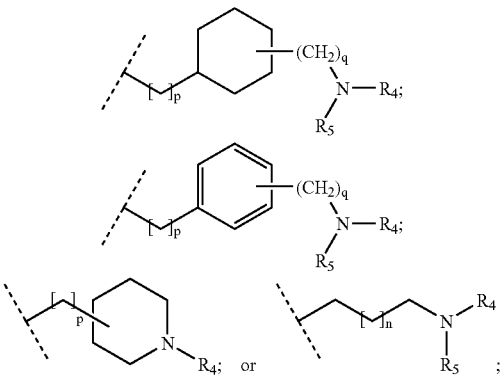

wherein:
- p is an integer from 1 to 3;
- q is an integer from 0 to 3;
- n is an integer from 0 to 5;

$R_4$, $R_5$ are each independently selected from:
- (L) hydrogen,
- (M) $C_{1-6}$alkyl optionally and independently substituted with one or more of the following groups (i) to (ix), or wherein $R_4$ and $R_5$ together constitute a methylene bridge which together with the nitrogen atom between them forms a four to six-membered ring wherein one of the methylene groups is optionally replaced by an oxygen, sulfur or NR group, wherein R is hydrogen or $C_{1-6}$alkyl, and said ring is optionally substituted with one or more of the following groups (i) to (ix):
  - (i) hydroxyl,
  - (ii) $C_{1-6}$alkyloxy,
  - (iii) $C_{1-6}$alkylthio,
  - (iv) halogen,
  - (v) aryl,
  - (vi) heteroaryl,
  - (vii) —$COR_{19}$, wherein $R_{19}$ is:
    - (a) $C_{1-6}$alkyl,
    - (b) $C_{1-6}$alkyloxy,
    - (c) —$NR_{20}R_{21}$, wherein $R_{20}$ and $R_{21}$ are each independently selected from:
      - (I) hydrogen,
      - (II) $C_{1-6}$alkyl,
      - (III) aryl,
      - (IV) heteroaryl,
      - (V) or wherein $R_{20}$ and $R_{21}$ together constitute a methylene bridge which together with the nitrogen atom between them forms a four to six-membered ring, wherein one of the methylene groups is optionally replaced by an oxygen, sulfur or NR group, wherein R is hydrogen or $C_{1-6}$alkyl,
  - (viii) —$SO_2R_{22}$, wherein $R_{22}$ is selected from:
    - (a) $C_{1-6}$alkyl,
    - (b) aryl,
    - (c) —$NR_{23}R_{24}$, wherein $R_{23}$ and $R_{24}$ are each independently selected from:
      - (I) hydrogen,
      - (II) $C_{1-6}$alkyl,
      - (III) aryl,
      - (IV) heteroaryl
  - (ix) —$NR_{25}R_{26}$, wherein $R_{25}$ and $R_{26}$ are each independently selected from:
    - (a) hydrogen,
    - (b) $C_{1-6}$alkyl,
    - (c) aryl, (d) heteroaryl, (e) —COR$_{27}$, wherein R$_{27}$ is:
  (I) C$_{1-6}$alkyl,
  (II) C$_{1-6}$alkyloxy,
  (III) —NR$_{28}$R$_{29}$, wherein R$_{28}$ and R$_{29}$ are each independently selected from:
    (1) hydrogen,
    (2) C$_{1-6}$alkyl,
    (3) aryl,
    (4) heteroaryl, and
    (5) or wherein R$_{28}$ and R$_{29}$ together constitute a methylene bridge which together with the nitrogen atom between them forms a four to six-membered ring, wherein one of the methylene groups is optionally replaced by an oxygen, sulfur or NR group, wherein R is hydrogen or C$_{1-6}$alkyl;

(f) —SO$_2$R$_{30}$, wherein R$_{30}$ is selected from:
  (I) C$_{1-6}$alkyl,
  (II) aryl, and
  (III) heteroaryl, or a tautomer thereof, or a pharmaceutically acceptable salt thereof, or a compound of formula I where one or more amino groups are protected by an amino-protecting group.

2. A compound according to claim 1, wherein:
X is —CH$_2$—, —CH$_2$—CH$_2$— or —CH$_2$—CH$_2$—CH$_2$—;
Y is —NH—;
R$_1$ is selected from aryl optionally and independently substituted with one or more of the following groups:
  (A) C$_{1-6}$alkoxy or C$_{1-6}$alkylthio, each optionally substituted with halogen,
  (B) halogen,
R$_2$ is selected from the following groups:
  (A) cyano,
  (B) —CONH$_2$, or
  (C) nitro;
R$_3$ is:

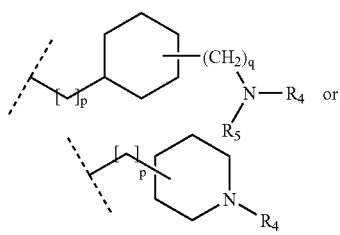

wherein:
p is 1 or 2,
q is 0, 1 or 2,
R$_4$, R$_5$ are hydrogen or C$_{1-6}$alkyl, or wherein R$_4$ and R$_5$ together constitute a methylene bridge which together with the nitrogen atom between them forms a four or five-membered ring which is optionally and independently substituted with a hydroxyl group;
or a tautomer thereof, or a pharmaceutically acceptable salt thereof, or a compound of formula I where one or more amino groups are protected by an amino-protecting group.

3. A compound according to claim 1, having the following formula (II):

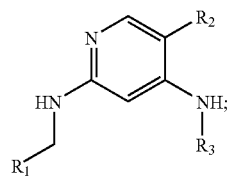

wherein,
R$_1$ is phenyl, optionally and independently substituted with one or two of the following groups:
  (A) —OCF$_3$,
  (B) halogen,
R$_2$ is selected from the following groups:
  (A) cyano, or
  (B) nitro;
R$_3$ is:

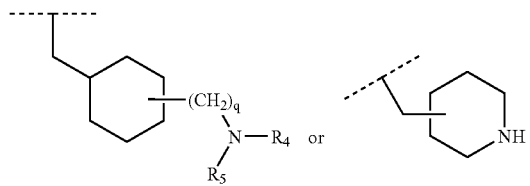

wherein:
q is 0 or 1,
R$_4$, R$_5$ are hydrogen or, wherein R$_4$ and R$_5$ together constitute a methylene bridge which together with the nitrogen atom between them forms a four or five-membered ring which is optionally substituted with a hydroxyl group,
or a tautomer thereof, or a pharmaceutically acceptable salt thereof, or a compound of formula I where one or more amino groups are protected by an amino-protecting group.

4. A compound according to claim 1, having the following formula (III):

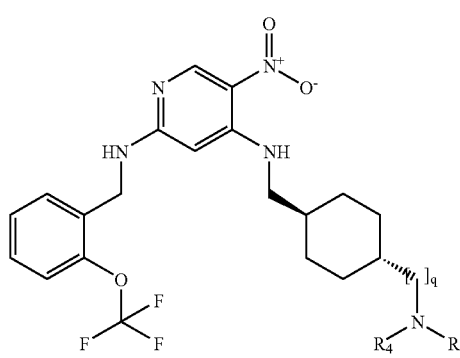

wherein,
q is 0 or 1.
R$_4$, R$_5$ are hydrogen or wherein R$_4$ and R$_5$ together constitute a methylene bridge which together with the nitrogen atom between them forms a four or five-membered ring which is optionally substituted with a hydroxyl group,
or a tautomer thereof, or a pharmaceutically acceptable salt thereof, or a compound of formula I where one or more amino groups are protected by an amino-protecting group.

5. A compound according to claim 1, selected from the following compounds:
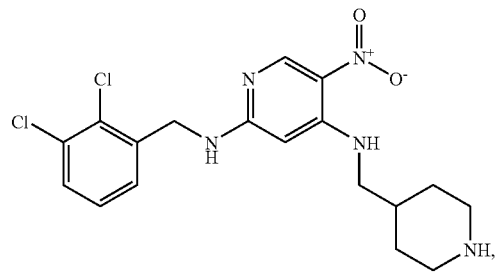
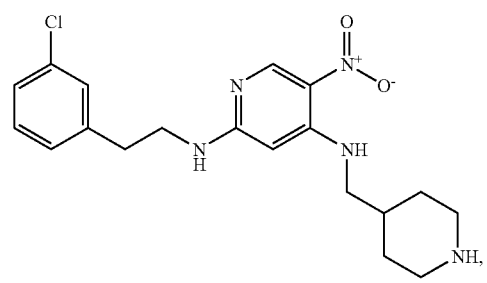
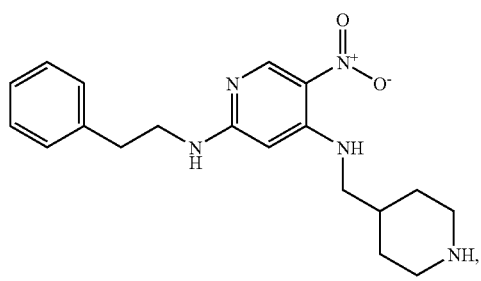
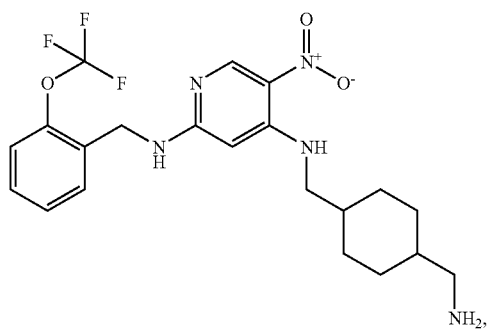
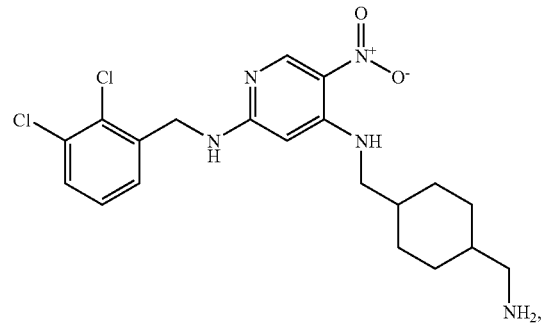
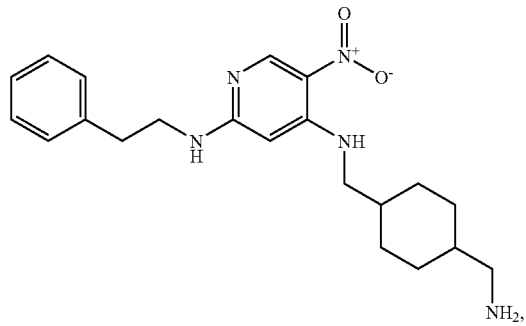
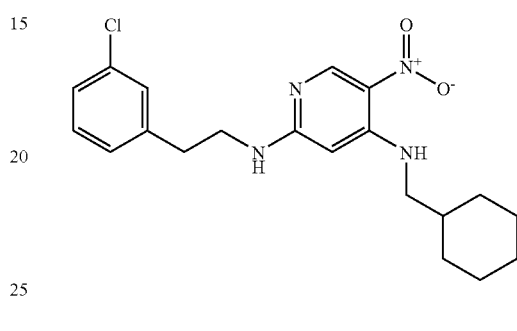
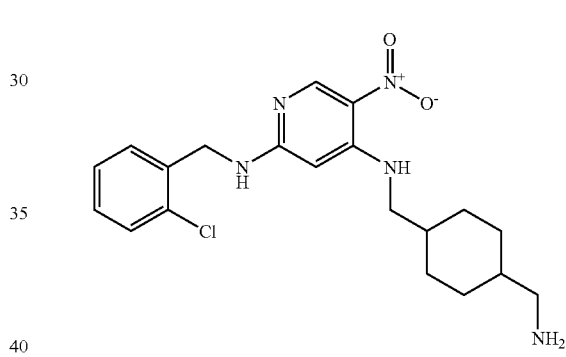
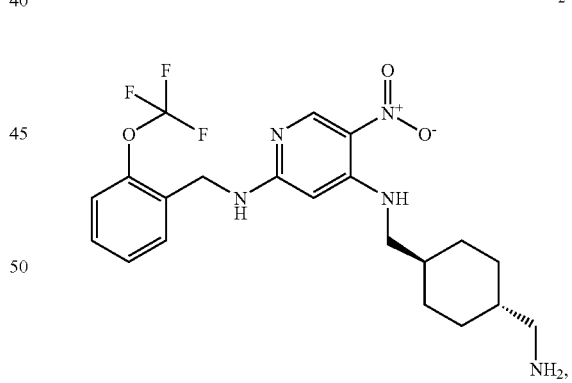
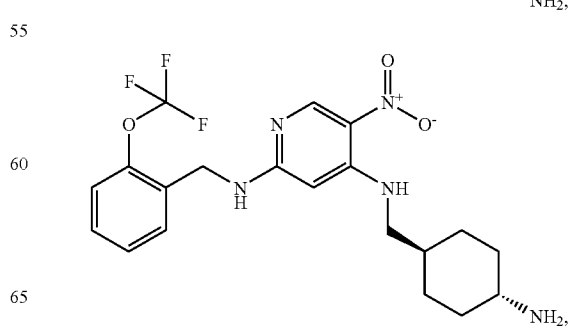

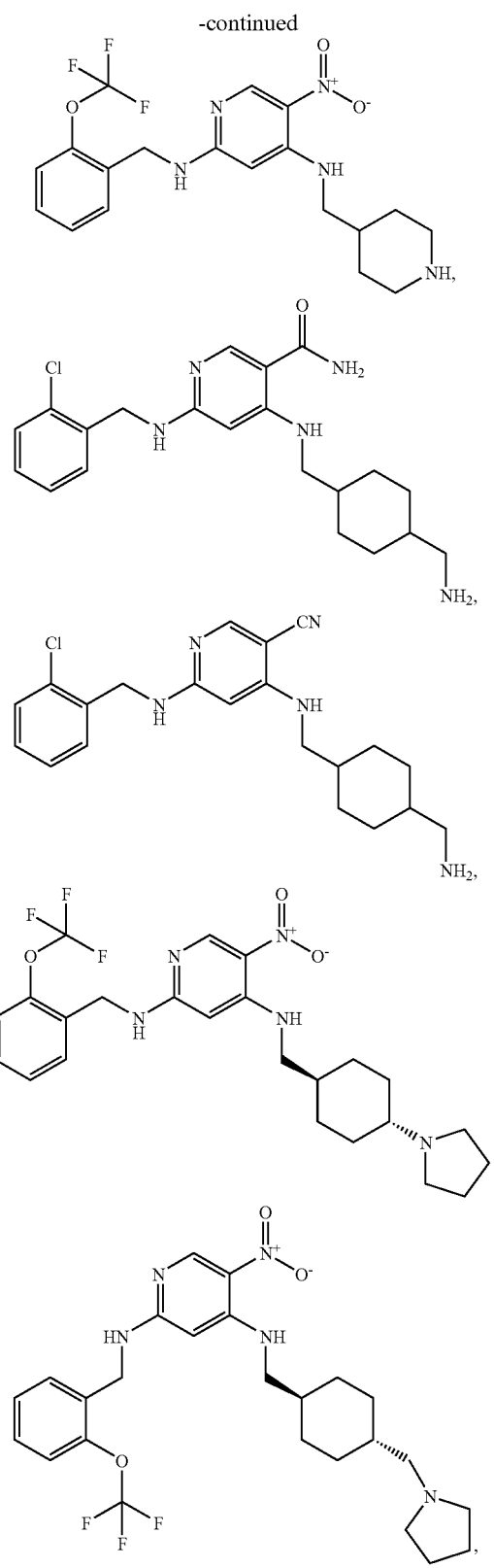
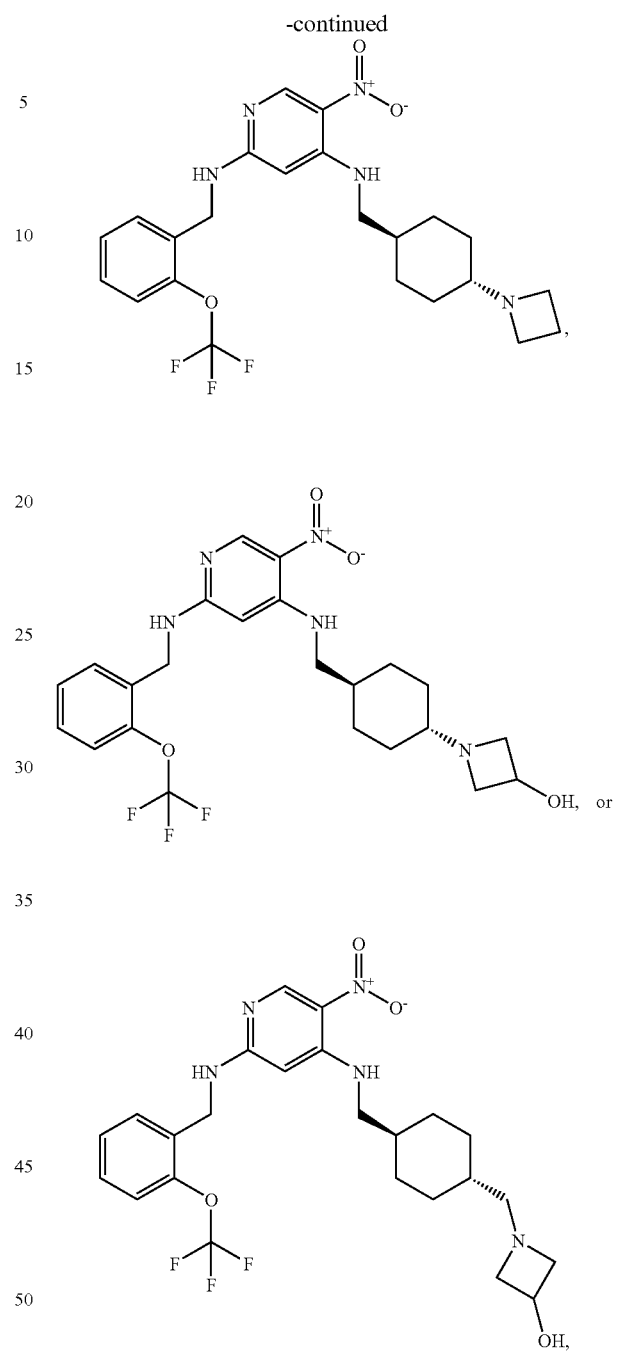
or a pharmaceutically acceptable salt thereof.
6. A pharmaceutical composition comprising a compound according to claim 1, and at least one pharmaceutically acceptable carrier or adjuvant.
* * * * *